(12) United States Patent
Ross et al.

(10) Patent No.: US 12,376,920 B2
(45) Date of Patent: Aug. 5, 2025

(54) STEERING ASSEMBLY FOR SURGICAL ROBOT

(71) Applicant: MAKO Surgical Corp., Weston, FL (US)

(72) Inventors: Alan Ross, Albuquerque, NM (US); Paul Shiels, Albuquerque, NM (US)

(73) Assignee: MAKO Surgical Corp., Weston, FL (US)

( * ) Notice: Subject to any disclaimer, the term of this patent is extended or adjusted under 35 U.S.C. 154(b) by 0 days.

(21) Appl. No.: 18/124,272

(22) Filed: Mar. 21, 2023

(65) Prior Publication Data

US 2023/0218355 A1     Jul. 13, 2023

Related U.S. Application Data

(63) Continuation of application No. 17/666,811, filed on Feb. 8, 2022, now Pat. No. 11,638,620, which is a (Continued)

(51) Int. Cl.
    *A61G 5/06*     (2006.01)
    *A61B 34/30*     (2016.01)
    (Continued)

(52) U.S. Cl.
    CPC .............. *A61B 34/30* (2016.02); *A61B 50/13* (2016.02); *A61B 2560/0431* (2013.01);
    (Continued)

(58) Field of Classification Search
    CPC . A61B 34/30; A61B 50/13; A61B 2560/0431; A61B 2560/0437;
    (Continued)

(56) References Cited

U.S. PATENT DOCUMENTS 2,042,489 A     6/1936    Williams
2,459,066 A *   1/1949    Duke ........................ A61H 3/04
                                                     297/5

(Continued)

FOREIGN PATENT DOCUMENTS

CN       201261483 Y     6/2009
CN       102892372       1/2013

(Continued)

OTHER PUBLICATIONS

International Search Report and Written Opinion for PCT Application No. PCT/US2016/050189, mailed Oct. 20, 2016, 11 pages.

(Continued)

*Primary Examiner* — Alentin Neacsu
*Assistant Examiner* — Felicia L. Brittman-Alabi
(74) *Attorney, Agent, or Firm* — FOLEY & LARDNER LLP

(57) ABSTRACT

A surgical robot a robotic device and a cart. The cart is coupled to the robotic device and includes a steering assembly. The steering assembly includes wheels and is configured such that the wheels allow the cart to roll in a linear direction when a first mode is selected and the wheels allow the cart to roll in a rotational direction when a second mode is selected.

15 Claims, 28 Drawing Sheets

Related U.S. Application Data continuation of application No. 16/793,076, filed on Feb. 18, 2020, now Pat. No. 11,278,363, which is a continuation of application No. 15/256,273, filed on Sep. 2, 2016, now Pat. No. 10,603,119.

(60) Provisional application No. 62/214,718, filed on Sep. 4, 2015, provisional application No. 62/214,696, filed on Sep. 4, 2015.

(51) Int. Cl.
    *A61B 50/13*     (2016.01)
    *B62B 3/00*     (2006.01)
    *B62B 3/02*     (2006.01)
    *B62B 3/10*     (2006.01)
    *B62B 5/04*     (2006.01)

(52) U.S. Cl.
CPC ....... *A61B 2560/0437* (2013.01); *B62B 3/001* (2013.01); *B62B 3/02* (2013.01); *B62B 3/10* (2013.01); *B62B 5/0433* (2013.01); *B62B 5/0457* (2013.01); *B62B 5/049* (2013.01)

(58) Field of Classification Search
CPC .. B62B 3/001; B62B 3/02; B62B 3/10; B62B 5/0433; B62B 5/0457; B62B 5/049
USPC ........................................................ 180/19.1
See application file for complete search history.

(56) References Cited

U.S. PATENT DOCUMENTS

| | | | |
|---|---|---|---|
| 2,537,909 A | 1/1951 | Puddester | |
| 2,624,590 A | 1/1953 | Tilton | |
| 2,843,392 A | 7/1958 | Simpkins | |
| 3,057,426 A | 10/1962 | Hastings, Jr. | |
| 3,181,640 A | 5/1965 | Goodacre et al. | |
| 3,250,513 A | 5/1966 | Fenner et al. | |
| 4,341,279 A | 7/1982 | Waerve | |
| 5,081,662 A | 1/1992 | Warden et al. | |
| 5,318,313 A | 6/1994 | Chapman | |
| 5,957,649 A | 9/1999 | English et al. | |
| 6,520,642 B1 | 2/2003 | Chapman | |
| 6,543,798 B2 | 4/2003 | Schaffner et al. | |
| 6,659,706 B2 | 12/2003 | English et al. | |
| 6,736,584 B2 | 5/2004 | Dehn et al. | |
| 6,814,490 B1 * | 11/2004 | Suhm | A61B 6/547 378/198 |
| 6,837,665 B2 | 1/2005 | English et al. | |
| 6,843,625 B2 | 1/2005 | Hewitt | |
| 7,112,028 B2 | 9/2006 | English et al. | |
| 7,533,892 B2 | 5/2009 | Schena et al. | |
| 7,686,107 B1 | 3/2010 | Bland et al. | |
| 7,909,122 B2 | 3/2011 | Schena et al. | |
| 7,926,131 B2 | 4/2011 | Menkedick et al. | |
| 8,365,353 B2 | 2/2013 | Block et al. | |
| 8,448,729 B2 | 5/2013 | Schena et al. | |
| 8,511,693 B2 | 8/2013 | Gass et al. | |
| 8,528,685 B2 | 9/2013 | Scherbring et al. | |
| 8,602,136 B2 * | 12/2013 | Altena | A61G 5/04 180/19.1 |
| 8,621,690 B2 | 1/2014 | Hornbach et al. | |
| 8,833,709 B2 | 9/2014 | Weng | |
| 8,919,464 B2 | 12/2014 | Greenwood et al. | |
| 9,101,348 B2 | 8/2015 | Griffiths et al. | |
| 9,215,968 B2 | 12/2015 | Schostek et al. | |
| 9,296,405 B2 | 3/2016 | Lenkman et al. | |
| 9,308,937 B2 | 4/2016 | Griffiths et al. | |
| 2003/0019682 A1 | 1/2003 | Schaedler et al. | |
| 2003/0205878 A1 | 11/2003 | Martis et al. | |
| 2005/0072621 A1 | 4/2005 | Hara et al. | |
| 2005/0134011 A1 | 6/2005 | Lin | |
| 2007/0106128 A1 | 5/2007 | Lavallee | |
| 2007/0163816 A1 * | 7/2007 | Schena | A61B 34/30 180/19.1 |
| 2008/0056871 A1 | 3/2008 | Morgan et al. | |
| 2008/0122227 A1 | 5/2008 | Hammerle | |
| 2009/0199674 A1 | 8/2009 | Schena et al. | |
| 2010/0191405 A1 | 7/2010 | Sugitani et al. | |
| 2011/0073725 A1 | 3/2011 | Aoyama | |
| 2012/0248719 A1 | 10/2012 | Rossini et al. | |
| 2013/0110128 A1 | 5/2013 | Schostek et al. | |
| 2013/0113171 A1 | 5/2013 | Pennings et al. | |
| 2014/0034357 A1 | 2/2014 | Lee et al. | |
| 2014/0188132 A1 | 7/2014 | Kang | |
| 2014/0343570 A1 | 11/2014 | Schena et al. | |
| 2017/0065355 A1 | 3/2017 | Ross et al. | |

FOREIGN PATENT DOCUMENTS

| | | | |
|---|---|---|---|
| CN | 202935406 U | | 5/2013 |
| CN | 205044782 | | 2/2016 |
| DE | 10305122 A1 | | 8/2004 |
| EP | 2 418 137 | | 2/2012 |
| JP | H10-155838 A | | 6/1998 |
| JP | 2016022756 A | * | 2/2016 |
| KR | 101376544 B1 | * | 3/2014 |
| WO | WO-2008/025901 A2 | | 3/2008 |
| WO | WO-2011/120083 A1 | | 10/2011 |
| WO | WO-2013/054357 A2 | | 4/2013 |
| WO | WO-2014/143890 A1 | | 9/2014 |
| WO | WO-2014/151642 | | 9/2014 |
| WO | WO-2014/151744 A1 | | 9/2014 |

OTHER PUBLICATIONS

International Search Report and Written Opinion for PCT Application No. PCT/US2016/050233, mailed Oct. 20, 2016, 11 pages.
Janssen, Tim, "Rolling Lift for a Workbench," taken from https://www.finewoodworking.com/2008/03/25/rolling-lift-for-a-workbench, dated Mar. 25, 2008, 5 pages.

* cited by examiner

STEERING ASSEMBLY FOR SURGICAL ROBOT

CROSS-REFERENCE TO RELATED PATENT APPLICATIONS

This application is a continuation of U.S. patent application Ser. No. 17/666,811, filed Feb. 8, 2022, which is a continuation of U.S. patent application Ser. No. 16/793,076, filed Feb. 18, 2020, which is a continuation of U.S. patent application Ser. No. 15/256,273, filed Sep. 2, 2016, which claims the benefit of and priority to U.S. Provisional Patent Application No. 62/214,696, filed Sep. 4, 2015, and U.S. Provisional Patent Application No. 62/214,718, filed Sep. 4, 2015, all of which are hereby incorporated by reference herein in their entireties.

BACKGROUND

The present invention relates generally to the field of carts for transportation of a robotic device and stability of the robotic device when in use.

Medical device carts may be used to transport a robotic device from one location to another. Traditional medical device carts have four wheels, two fixed front wheels and rear swiveling casters, which may provide adequate maneuverability during general transport, however maneuverability in an operating room has different needs. Space in the operating room is limited which makes navigating the cart around the operating room and into the proper position challenging. When pushing from a rear of the cart, controlling the direction of travel is challenging because of the leverage required to direct the front wheels. The cart has to be backed up, pivoted, and moved back in. Sometimes this has to be repeated several times until the position of the cart is correct. Sometimes, this requires handling the cart from a front end which may be in a sterile field of the operating room, which is not ideal. Further, during transport, the cart may encounter various uneven surfaces (e.g., ramps, inclines, etc.) that may increase the loading on an individual wheel of the cart and potentially cause a rocking or fluttering condition.

SUMMARY

According to one exemplary embodiment, a portable surgical robot includes a surgical device and a cart. The surgical device is coupled to the cart. The cart includes a chassis, a mount coupled to the chassis, a carriage pivotally coupled to the mount, and a set of wheels. The carriage includes a first bracket positioned at a first lateral end thereof and a second bracket positioned at a second lateral end thereof. A first wheel of the set of wheels is coupled to the first bracket and a second wheel of the set of wheels is coupled to the second bracket. The carriage is configured to pivot relative to the mount to prevent at least one of (i) rocking of the portable surgical robot, (ii) fluttering of the first wheel, (iii) fluttering of the second wheel, and (iv) tipping of the portable surgical robot.

According to another exemplary embodiment, a portable cart includes a chassis, a first wheeled mechanism coupled to a front portion of the chassis, and a second wheeled mechanism pivotably coupled to a rear portion of the chassis. The first wheeled mechanism and the second wheel mechanism facilitate maneuvering the portable cart. The second wheeled mechanism is configured to rotate relative to the chassis to prevent at least one of (i) rocking of the portable cart, (ii) fluttering of the first wheeled mechanism, (iii) fluttering of the second wheeled mechanism, and (iv) tipping of the portable cart.

According to still another exemplary embodiment, a pivoting carriage for a cart includes a mount, a pivoting member, and a set of wheels. The mount has a housing that defines an internal cavity and a pivot aperture. The mount is configured to couple to a chassis of the cart. The pivoting member is disposed within the internal cavity of the housing. The pivoting member includes a body having a first lateral end and a second lateral end, a first bracket positioned at the first lateral end of the body, a second bracket positioned at the second lateral end of the body, and a rod extending from the body. The rod is positioned to engage the pivot aperture of the housing to thereby pivotally couple the pivoting member to the mount such that the pivoting member is pivotally coupled to the chassis of the cart. The set of wheels includes a first wheel coupled to the first bracket and a second wheel coupled to the second bracket.

According to yet another exemplary embodiment, a pivoting carriage for a cart includes a frame member, a set of wheels, and a mount. The frame member includes a first bracket positioned at a first lateral end of thereof and a second bracket positioned at a second lateral end thereof. A first wheel is coupled to the first bracket and a second wheel is coupled to the second bracket. The mount is pivotably coupled to the frame member. The mount is configured to couple the pivoting carriage to a chassis of the cart. The frame member includes a pair of plates spaced a distance apart defining a cavity. The cavity is configured to receive the mount and facilitate rotation of the carriage relative to the mount.

Alternative exemplary embodiments relate to other features and combinations of features as may be generally recited in the claims.

BRIEF DESCRIPTION OF THE FIGURES

The disclosure will become more fully understood from the following detailed description, taken in conjunction with the accompanying figures, wherein like reference numerals refer to like elements, in which.

DETAILED DESCRIPTION

Figure 1:
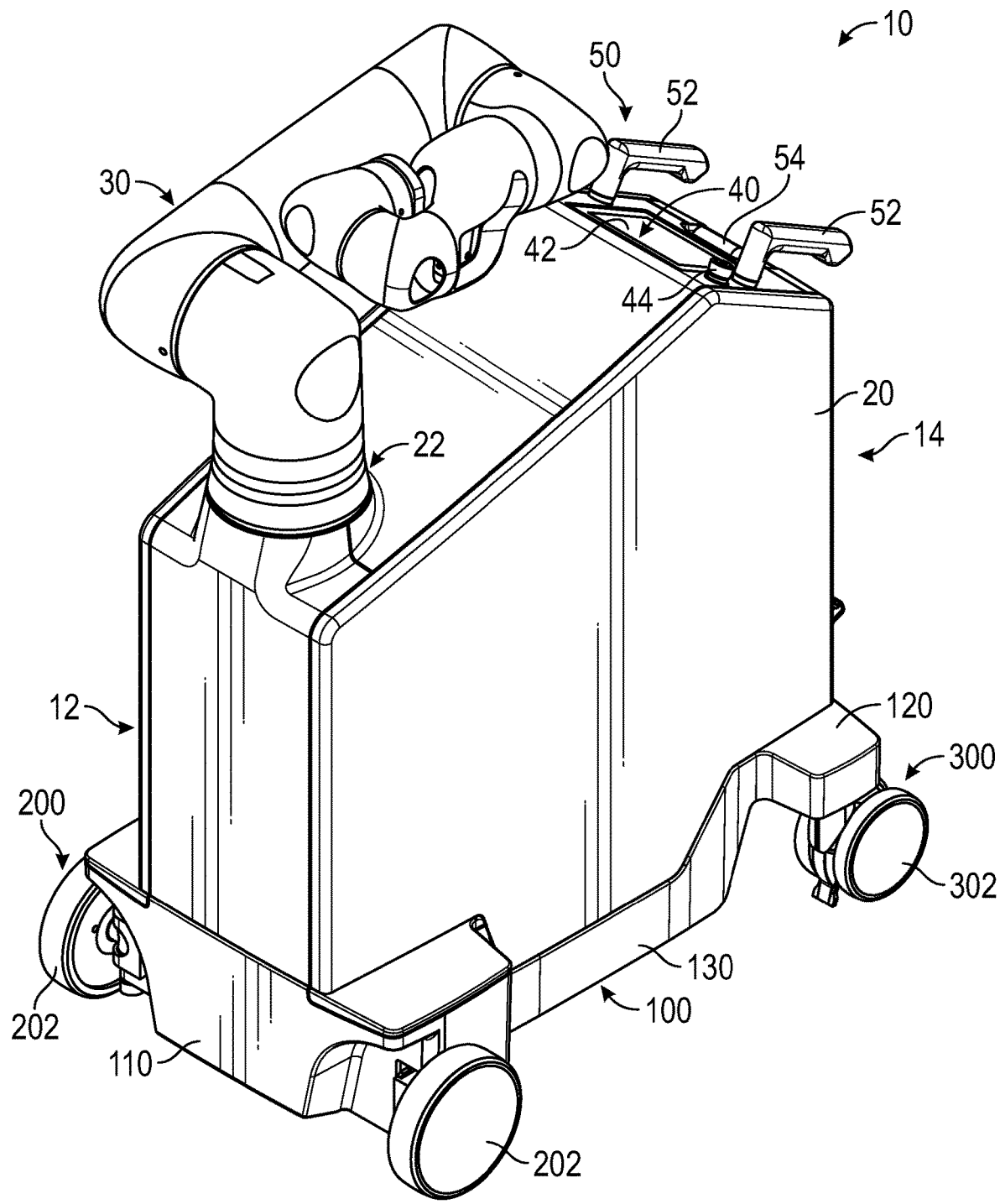
FIG. 1 is a front perspective view of a surgical cart, according to an exemplary embodiment.

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

The portable surgical cart described herein may be used in any context to maneuver and/or relocate a surgical device. The portable surgical cart may also include various features to aid in the stability of the cart during relocation (e.g., on ramps, uneven ground, over door frames, etc.) and during use of a surgical device (e.g., during an operation on a patient, during use of an articulating arm, etc.). In one embodiment, the portable surgical cart includes a steering assembly that facilitates moving the cart in any of a forward direction, a backward direction, a turning direction, a lateral direction, and a rotational direction. In some embodiments, the portable surgical cart includes a pivoting carriage assembly configured to self-adjust on uneven surfaces to increase stability of the portable surgical cart when stationary and/or in transit. In some embodiments, the portable surgical cart includes a locking mechanism configured to provide a support for the portable surgical cart when stationary to allow for precise and stable use of a surgical device of the portable surgical cart.

According to the exemplary embodiment shown in FIGS. 1-17B, a portable cart system, shown as surgical cart 10, includes a body 20; a chassis 100; a first wheeled mechanism, shown as wheel steering assembly 200, disposed at a front end 12 of the surgical cart 10; a second wheeled mechanism, shown as pivoting carriage assembly 300, disposed at a rear end 14 of the surgical cart 10; and a locking mechanism, shown as floor lock 400, disposed at the rear end 14 of the surgical cart 10.

As shown in FIGS. 1-3 and 10, the body 20 of the surgical cart 10 is coupled to the chassis 100. According to an exemplary embodiment, the body 20 is removably coupled to the chassis 100 (e.g., fastened, etc.). In an alternative embodiment, the body 20 is fixed to the chassis 100. For example, the body 20 and the chassis 100 may be welded or glued to one another during construction of the surgical cart 10. In another example, the body 20 and the chassis 100 may be a single, unitary structure. The wheel steering assembly 200 includes a pair of wheels, shown as front wheels 202, and the pivoting carriage assembly 300 includes a pair of caster wheels, shown as rear casters 302. The front wheels 202 and the rear casters 302 facilitate moving the surgical cart 10. According to an exemplary embodiment, the surgical cart 10 is configured to transport a surgical robotic device. In other embodiments, the cart is configured to transport a camera, a computer, a monitor, and/or any other device or component that may be used during a surgical procedure or medical monitoring. In alternative embodiments, the cart is configured for use as a guidance cart.

Figure 2:
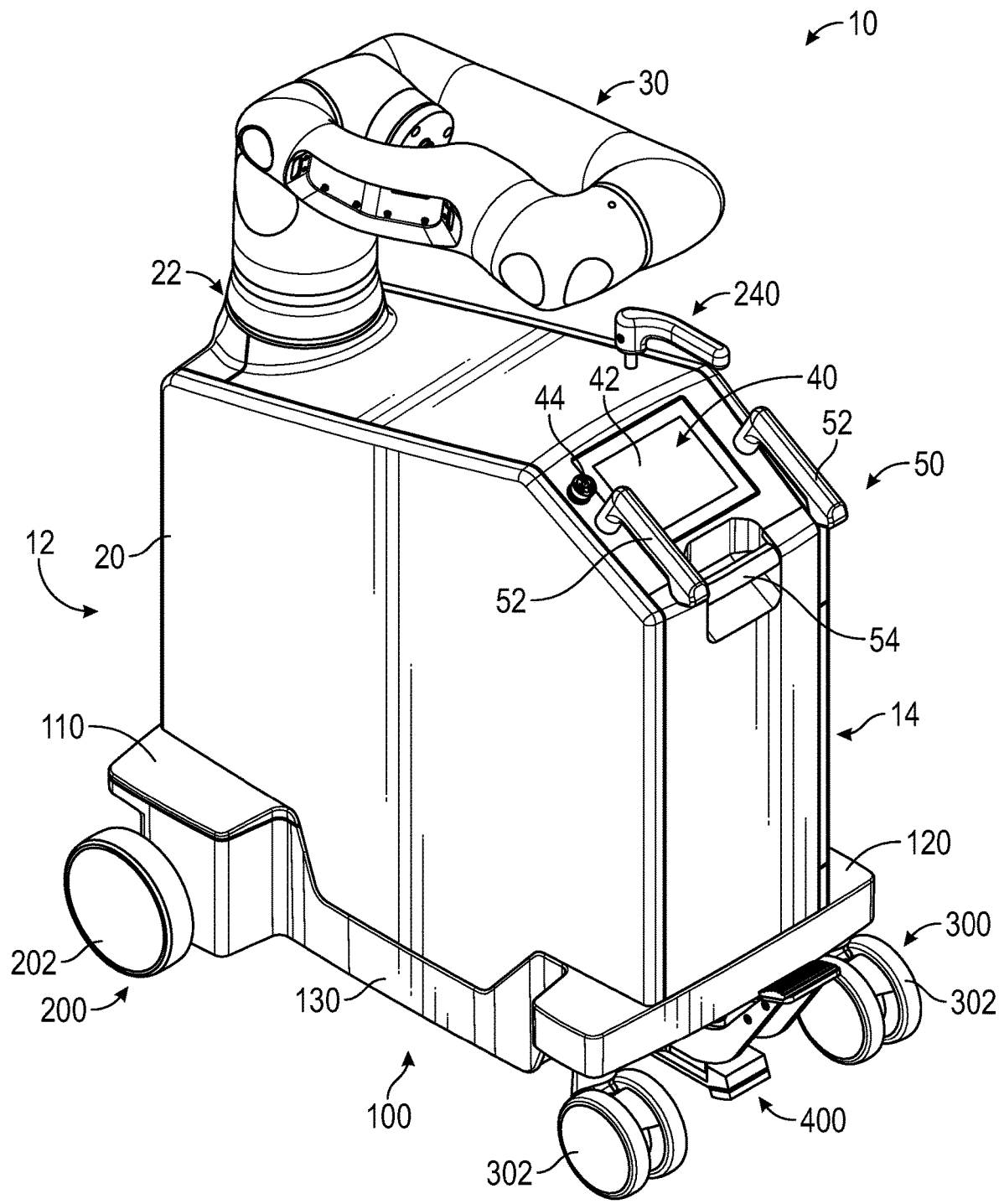
FIG. 2 is a left rear perspective view of the surgical cart of FIG. 1.
Figure 3:
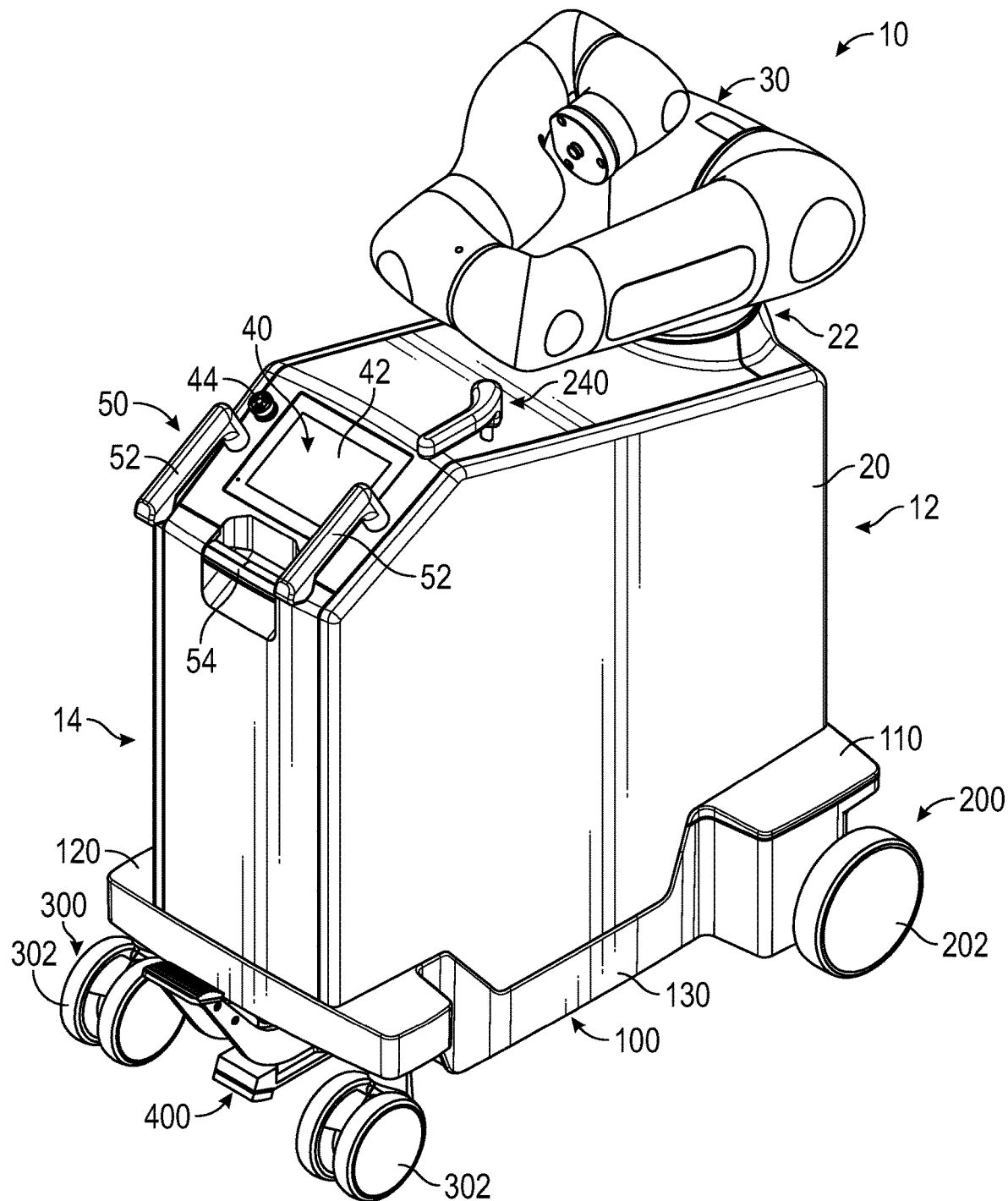
FIG. 3 is a right rear perspective view of the surgical cart of FIG. 1.

As shown in FIGS. 1-3 and 10, the body 20 of the surgical cart 10 may include a robotic device, shown as surgical device 30, a computing system 40, and a handle assembly 50. In some embodiments, the surgical cart 10 does not include the surgical device 30. For example, the surgical cart 10 may be a guidance cart and/or still another type of cart (e.g., a cart configured to transport a camera, a computer, a monitor, and/or any other device or component that may be used during a surgical procedure or medical monitoring, etc.). In one embodiment, the body 20 also includes various compartments (e.g., cabinets, drawers, etc.) configured to store various objects used in operation of the surgical cart 10 (e.g., surgical tools, etc.). As shown in FIGS. 1-3, the surgical device 30 is coupled (e.g., fastened, etc.) to a mounting location 22 defined by the body 20. The surgical device 30 may be any suitable mechanical or electromechanical structure. According to an exemplary embodiment, the surgical device 30 is an articulating arm (e.g., having three or more degrees of freedom or axes of movement, etc.). The computing system 40 may include various hardware components and software for operation and control of the surgical device 30. The computing system 40 may be any known computing system but is preferably a programmable, processor-based system. For example, the computing system 40 may include a microprocessor, a hard drive, random access memory (RAM), read only memory (ROM), input/output (I/O) circuitry, and any other well-known computer component. The computing system 40 is may be adapted for use with various types of storage devices (persistent and removable), such as, for example, a portable drive, magnetic storage (e.g., a floppy disk, etc.), solid state storage (e.g., a flash memory card, etc.), optical storage (e.g., a compact disc, etc.), and/or network/Internet storage.

The computing system 40 may be communicably coupled to the surgical device 30 via any suitable wired or wireless communication protocol (i.e., a physical interface). A physical interface may be any known interface such as, for example, a wired interface (e.g., serial, USB, Ethernet, CAN bus, and/or other cable communication interface) and/or a wireless interface (e.g., wireless Ethernet, wireless serial, infrared, and/or other wireless communication system). A software interface may enable the computing system 40 to communicate with and control operation of the surgical device 30. In one embodiment, the software interface includes a utility that allows the computing system 40 to issue commands to the surgical device 30. For example, the computing system 40 may provide a command to enter the surgical device into a specific mode (e.g., an autonomous mode, a haptic mode, a free mode, etc.). The computing system 40 may be adapted to enable the surgical device 30 to perform various functions related to surgical planning, navigation, image guidance, and/or haptic guidance. For example, the computing system 40 may include algorithms, programming, and software utilities related to general operation, data storage and retrieval, computer aided surgery (CAS), applications, haptic control, and/or any other suitable functionality.

In one embodiment, the surgical device 30 is configured as an autonomous surgical robotic system controlled by the computing system 40 to move a surgical tool to perform a procedure on a patient (e.g., for orthopedic joint replacement, to perform bone cutting autonomously with a high speed burr, etc.). In other embodiments, the surgical device 30 is a haptic device configured to be manipulated by a user to move a surgical tool to perform a procedure on a patient. For example, during a procedure, the computing system 40 may implement control parameters for controlling the surgical device 30 based on a relationship between an anatomy of the patient and a position, an orientation, a velocity, and/or an acceleration of a portion of the surgical device 30 (e.g., a surgical tool, etc.). In one embodiment, the surgical device 30 is controlled to provide a limit on user manipulation of the device (e.g., by limiting the user's ability to physically manipulate the surgical device 30, etc.). In another embodiment, the surgical device 30 is controlled to provide haptic guidance (i.e., tactile and/or force feedback) to the user. "Haptic" refers to a sense of touch, and the field of haptics involves research relating to human interactive devices that provide tactile and/or force feedback to an operator. Tactile feedback generally includes tactile sensations such as, for example, vibration, whereas force feedback refers to feedback in the form of force (e.g., resistance to movement, etc.) and/or torque (also known as "wrench"). Wrench may include feedback in the form of a force, a torque, or a combination of a force and a torque.

In orthopedic applications, for example, the surgical device 30 can be applied to the problems of inaccuracy, unpredictability, and non-repeatability in bone preparation by assisting the surgeon with proper sculpting of bone to thereby enable precise, repeatable bone resections while maintaining intimate involvement of the surgeon in the bone preparation process. Moreover, because the surgical device 30 may haptically guide the surgeon in the bone cutting operation or autonomously perform the operation, the skill level of the surgeon is less critical. As a result, surgeons with varying degrees of skill and experience are able to perform accurate, repeatable procedures.

As shown in FIGS. 1-3, the surgical cart 10 includes a display device 42 and an input device 44 disposed on the body 20 at the rear end 14 of the surgical cart 10. In an alternative embodiment, the display device 42 and/or the input device 44 are otherwise positioned on the surgical cart 10 or remote from the surgical cart 10 (e.g., mounted on a wall of an operating room or other location suitable for viewing by the user, etc.). The display device 42 is configured as a visual interface between the computing system 40 and the user. The display device 42 may be communicably coupled to the computing system 40 and may be any device suitable for displaying text, images, graphics, and/or other visual output. For example, the display device 42 may include a standard display screen (e.g., LED, LCD, CRT, plasma, etc.), a touch screen, a wearable display (e.g., eyewear such as glasses or goggles), a projection display, a head-mounted display, a holographic display, and/or any other visual output device. The display device 42 may be used to display any information useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy, tools, implants, etc.), digital or video images, registration information, calibration information, patient data, user data, measurement data, software menus, selection buttons, status information, and/or the like. The input device 44 may enable the user of the surgical cart 10 to communicate with the surgical device 30 and/or other components of the surgical cart 10 (e.g., the wheel steering assembly 200, the floor lock 400, etc.). The input device 44 may be communicably coupled to the computing system 40 and may include any device configured to enable a user to provide input the surgical cart 10. For example, the input device 44 may be, but not limited to, a keyboard, a mouse, a trackball, a touch screen, a touch pad, voice recognition hardware, dials, switches, buttons, a trackable probe, a foot pedal, a remote control device, a scanner, a camera, a microphone, a joystick, and/or the like. In some embodiments, the surgical cart 10 supplements or replaces direct visualization of a surgical site, enhances a surgeon's natural tactile sense and physical dexterity, and facilitates the targeting, repairing, and replacing of various structures in the body.

Referring to FIGS. 1-3 and 10, the handle assembly 50 may increase portability and maneuverability of the surgical cart 10. As shown in FIGS. 1-3 and 10, the handle assembly 50 is positioned at the rear end 14 of the surgical cart 10 and, in the embodiment shown, includes a pair of handles, shown as handgrips 52, and a handrail 54. The handgrips 52 and/or the handrail 54 may facilitate maneuvering the surgical cart 10 in at least one of a forward direction, a rearward direction, a lateral direction (i.e., a sideways direction), and a rotational direction. In alternative embodiments, the surgical cart 10 includes additional handles and/or handrails positioned around the body 20. In one embodiment, the handle assembly 50 includes a single, continuous structure that extends around the entire periphery of surgical cart 10 to provide 360 degree handhold access for ease of maneuverability of the surgical cart 10. In other embodiments, the handle assembly 50 includes a handrail positioned on one or both lateral sides of the surgical cart 10 to facilitate pulling or pushing the surgical cart 10 from the side (e.g., in a lateral direction, forward direction, rearward direction, etc.). In other embodiments, the handle assembly 50 includes a handrail positioned on the front end 12 of the surgical cart 10 to facilitate pulling or pushing the surgical cart 10 from the front end 12.

Figure 5A:
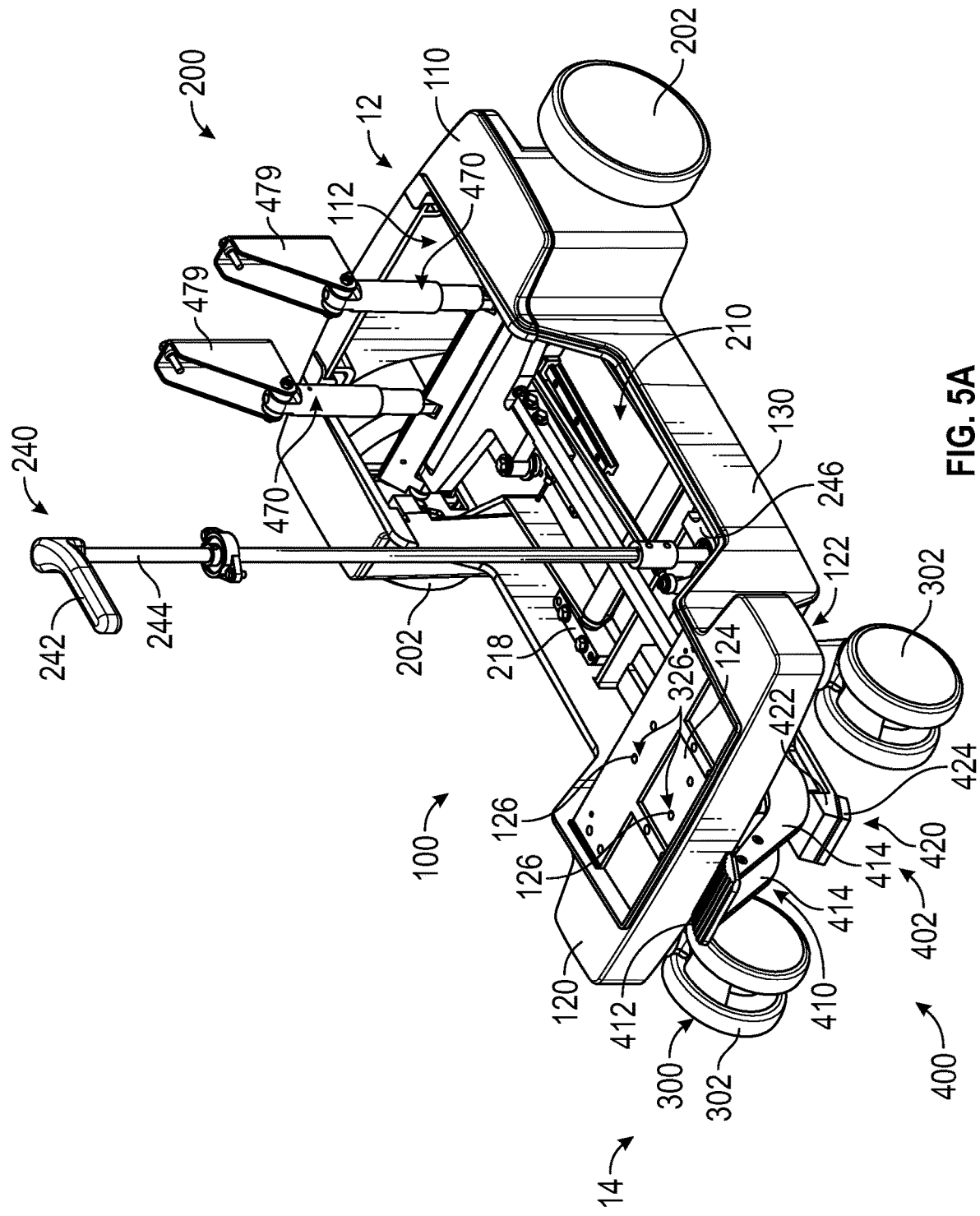
FIG. 5A is a perspective view of a chassis of the surgical cart of FIGS. 1-3 with a locking mechanism in a transport configuration, according to an exemplary embodiment.
Figure 5B:
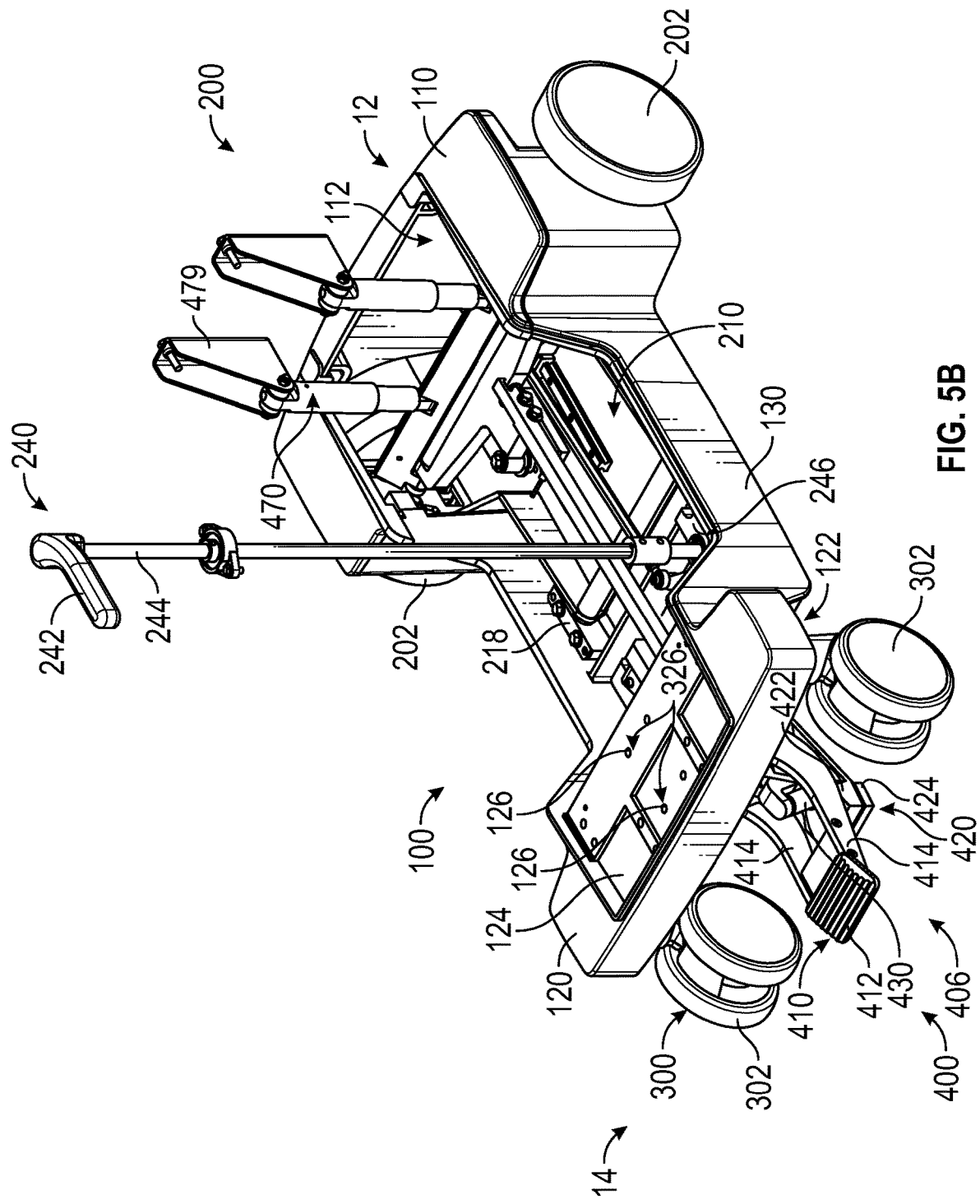
FIG. 5B is a perspective view of a chassis of the surgical cart of FIGS. 1-3 with a locking mechanism in a braked configuration, according to an exemplary embodiment.
Figure 11:
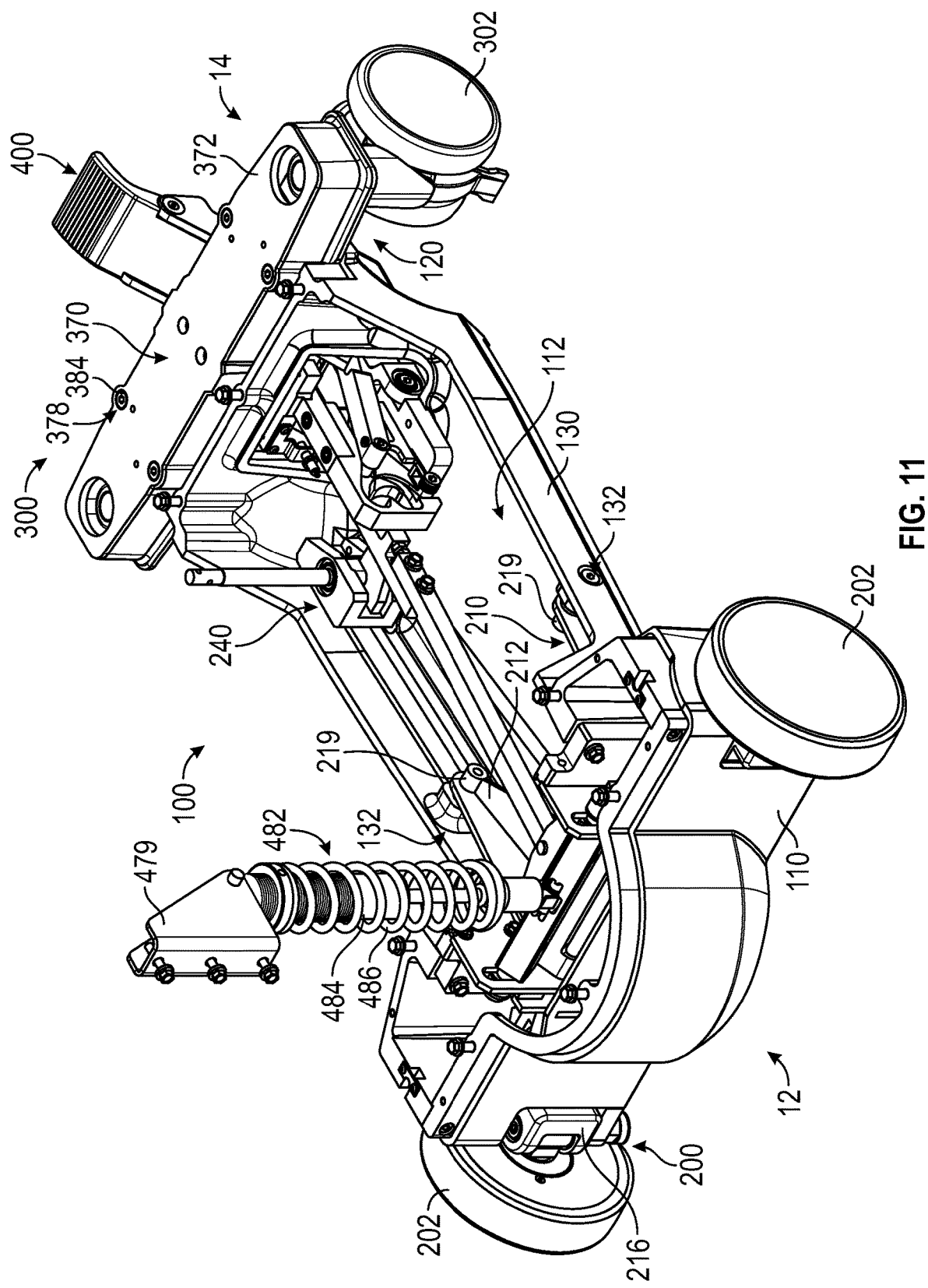
FIG. 11 is a perspective view of a chassis of the surgical cart of FIG. 10, according to an exemplary embodiment.

As shown in FIGS. 1-3, 5A-5B, and 10-11, the chassis 100 includes a front portion 110, a rear portion 120, and a middle portion 130. According to an exemplary embodiment, the front portion 110 is coupled to the rear portion 120 via the middle portion 130 to create a single, continuous chassis 100 (i.e., a unitary structure). As shown in FIGS. 5A-5B and 11, the front portion 110 and the middle portion 130 of the chassis 100 define an inner volume 112. The inner volume 112 is configured to receive the wheel steering assembly 200 such that the wheel steering assembly 200 may be coupled to the chassis 100. The rear portion 120 of the chassis 100 defines a cavity 122. The cavity 122 is configured to receive the pivoting carriage assembly 300 such that the pivoting carriage assembly 300 may be coupled to the chassis 100.

As shown in FIGS. 4A-4D, the pivoting carriage assembly 300 includes a frame member, shown as pivoting carriage 310. The pivoting carriage 310 includes a pair of brackets, shown as caster brackets 312. The caster brackets 312 are configured to couple the rear casters 302 to the pivoting carriage 310. The rear casters 302 include an extension, shown as stem 304, that extends from a top portion thereof. The caster brackets 312 are configured to receive the stems 304 of the rear casters 302 to rotationally couple the rear casters 302 to the pivoting carriage 310. In an alternative embodiment, the pivoting carriage 310 defines a flat mounting location and the rear casters 302 include a corresponding flat mounting plate configured to be fastened to the flat mounting location to couple the rear casters 302 to the pivoting carriage 310. According to an exemplary embodiment, the rear casters 302 are rotationally coupled to the pivoting carriage 310 such that the rear casters 302 are free to rotate about a central axis thereof, shown as vertical axis 340. Thus, the rear casters 302 may freely rotate about vertical axis 340 as the surgical cart 10 is maneuvered. In some embodiments, the rear casters 302 include a brake to prevent rotation of wheels of the rear casters 302 (i.e., aid in locking the surgical cart 10 in place) and/or rotationally fix the rear casters 302 in a desired direction (i.e., prevent rotation about the vertical axis 340). In an alternative embodiment, the rear casters 302 are rotationally fixed relative to the vertical axis 340 such that they are oriented in a single direction (e.g., forward, etc.).

Referring still to FIGS. 4A-4D, the pivoting carriage assembly 300 includes a mounting portion, shown as carriage mount 320. According to an exemplary embodiment, the carriage mount 320 is configured to pivotably couple the pivoting carriage assembly 300 to the rear portion 120 of the chassis 100. As shown in FIGS. 4A-4D, the carriage mount 320 includes a top surface, shown as mounting surface 322, and side surfaces, shown as interaction surfaces 328. According to the exemplary embodiment shown in FIGS. 4A-4D, the carriage mount 320 defines a plurality of apertures, shown as apertures 325, configured to receive a corresponding plurality of fasteners, shown as fasteners 326, that extend from the mounting surface 322. In an alternative embodiment, the fasteners 326 are integrally formed along the mounting surface 322 of the carriage mount 320.

Referring back to FIGS. 5A-5B, the rear portion 120 of the chassis 100 includes a plate, shown as mounting plate 124. The mounting plate 124 defines a plurality of apertures, shown as apertures 126. The apertures 126 are positioned to correspond with the fasteners 326 of the carriage mount 320 to facilitate coupling the pivoting carriage assembly 300 to the chassis 100. According to an exemplary embodiment, the pivoting carriage assembly 300 is recessed within the cavity 122 such that the mounting surface 322 of the carriage mount 320 abuts a bottom surface of mounting plate 124. In one embodiment, the apertures 126 are threaded such that an additional corresponding fastener (e.g., nut, etc.) is not needed when the apertures 126 receive the fasteners 326 (e.g., bolts, etc.). In other embodiments, the fasteners 326 extend through the apertures 126 and receive corresponding fasteners (e.g., nuts, etc.) to couple the pivoting carriage assembly 300 to the chassis 100. In still another embodiment, fasteners (e.g., nuts, etc.) are fixed (e.g., welded, glued, integrally formed, etc.) to the mounting plate 124, positioned to align with the apertures 126 and receive the fasteners 326.

Referring back to FIGS. 4A-4D, the pivoting carriage 310 defines a pair of apertures, shown as apertures 314. The apertures 314 are configured to receive a rod, shown as pivoting rod 324, that extends from each longitudinal end of the carriage mount 320, thereby pivotably coupling the carriage mount 320 and the pivoting carriage 310. The interaction between the apertures 314 and the pivoting rod 324 facilitates the rotation of the pivoting carriage 310 about a longitudinal axis, shown as longitudinal axis 330. In some embodiments, the rotation of the pivoting carriage 310 about the longitudinal axis 330 is aided by a lubricant and/or a bearing disposed between the apertures 314 and the pivoting rod 324.

As shown in FIGS. 4A-4D, the pivoting carriage 310 includes a pair of plates, shown as plates 316, disposed on each lateral side of the carriage mount 320. The plates 316 are spaced a distance apart to define a cavity, shown as pivoting gap 318. The pivoting gap 318 is configured to receive the carriage mount 320 when the carriage mount 320 is coupled to the pivoting carriage 310 (e.g., rotationally coupled via the pivoting rod 324, etc.). According to an exemplary embodiment, the pivoting gap 318 is sized to facilitate the rotation of the pivoting carriage 310 relative to the carriage mount 320.

Figure 4A:
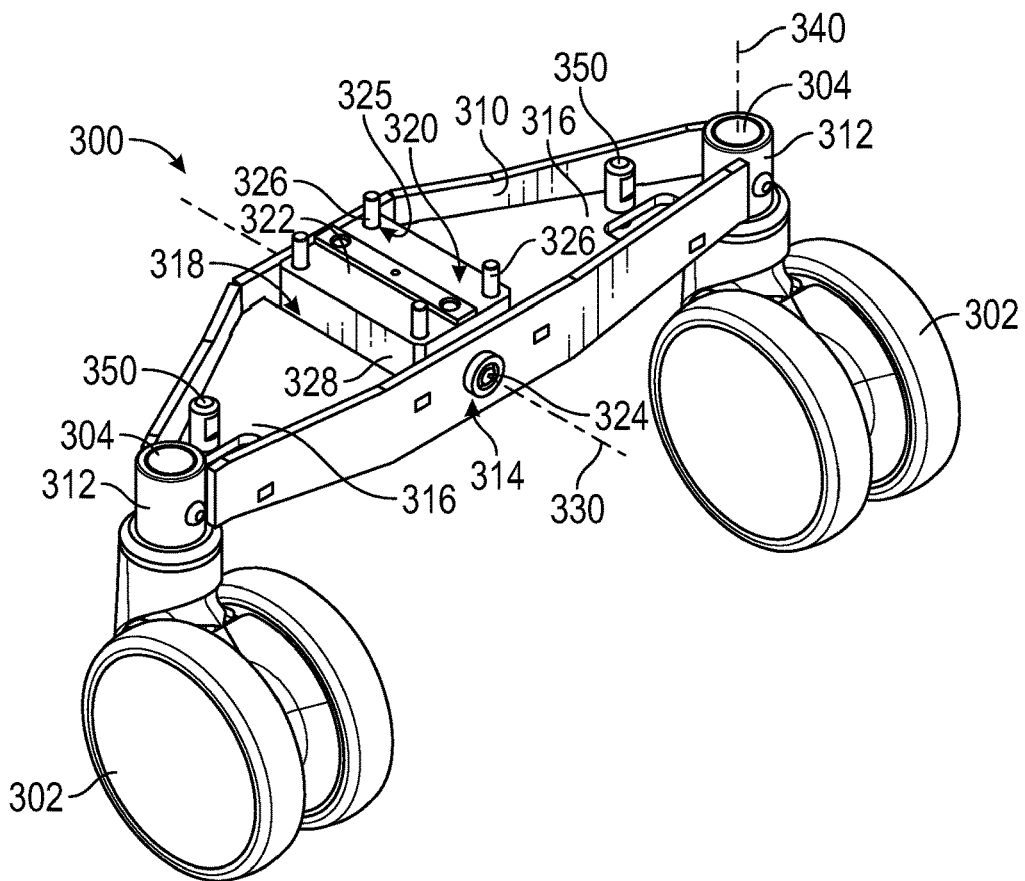
FIGS. 4A-4D are various views of a pivoting carriage assembly of the surgical cart of FIGS. 1-3, according to an exemplary embodiment.
Figure 4B:
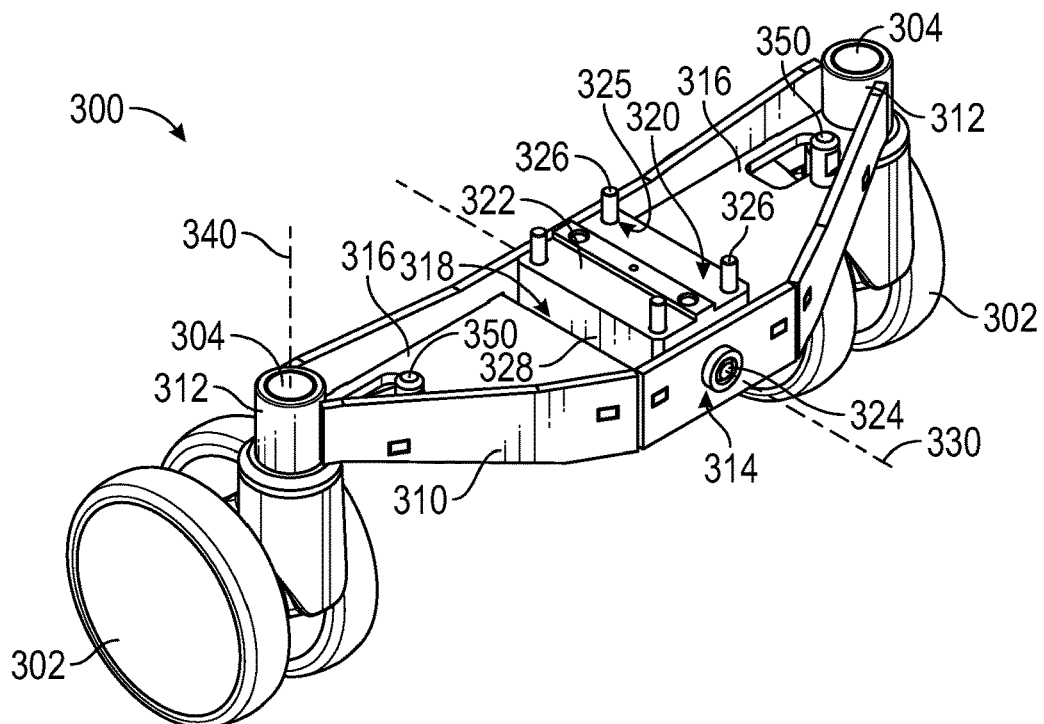
Figure 4C:
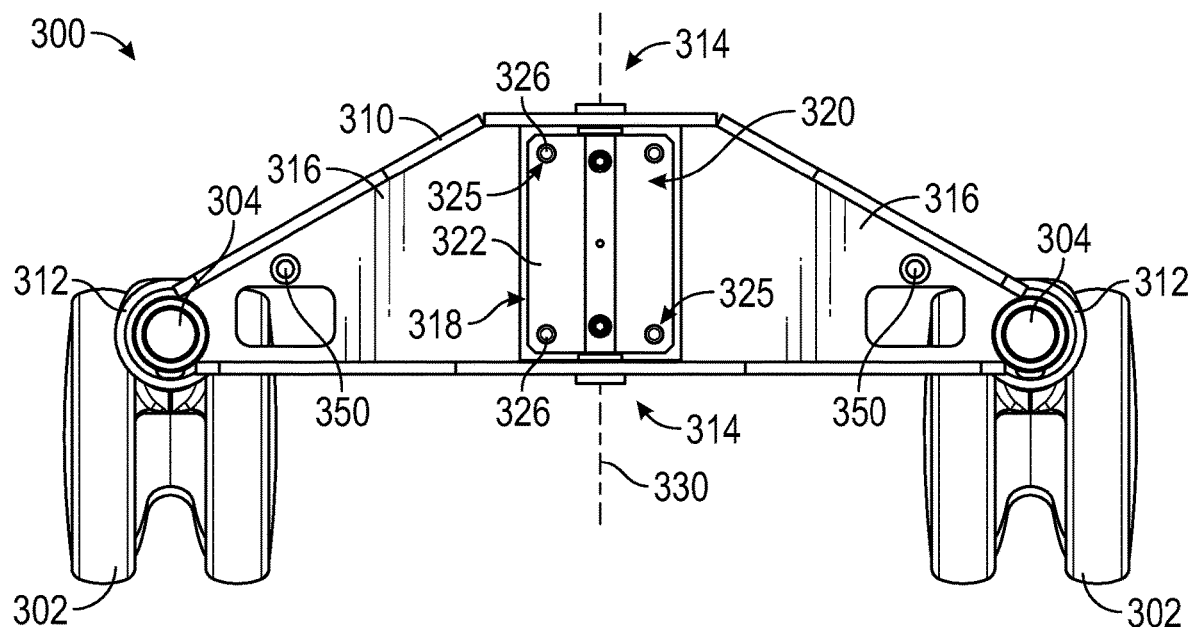
Figure 4D:
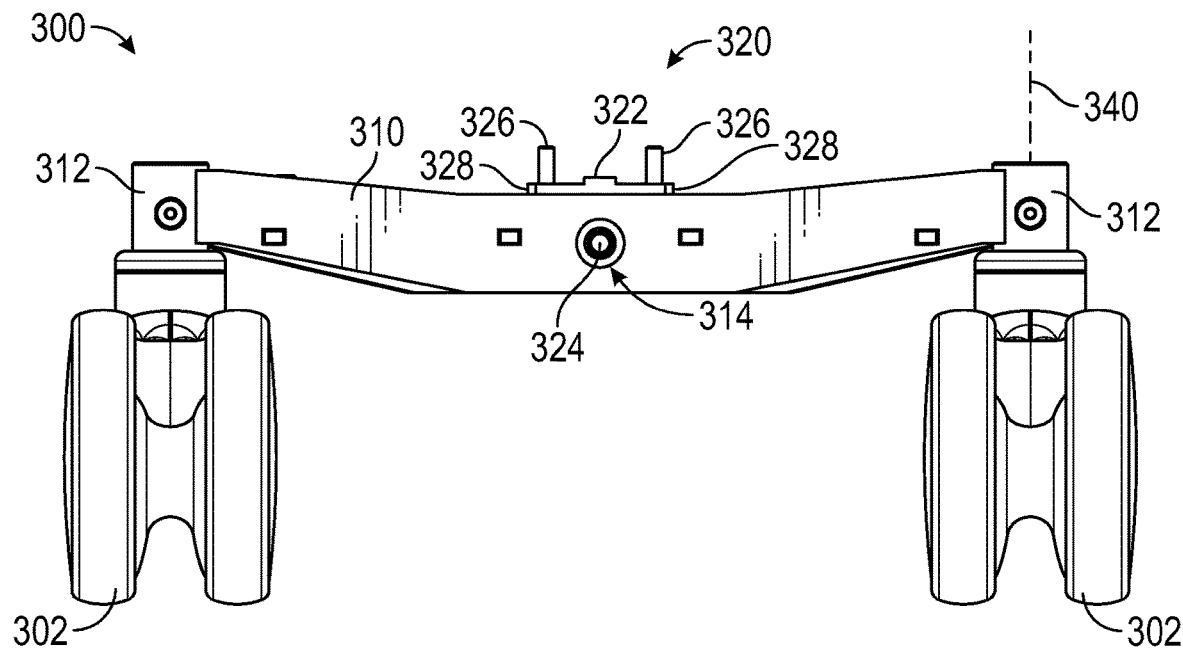

As shown in FIGS. 4A-4C, the pivoting carriage assembly 300 includes a limiting member, shown as rotational stop 350, positioned on each lateral side of the pivoting carriage 310. In other embodiments, the pivoting carriage assembly 300 includes a different number of rotational stops 350 on each lateral side of the pivoting carriage 310 (e.g., two, three, etc.). As shown in FIGS. 4A-4C, the rotational stops 350 are disposed along the plates 316. In one embodiment, the rotational stops 350 are coupled to the plates 316 (e.g., welded, glued, fastened, etc.). In an alternative embodiment, the rotational stops 350 and the plates 316 form a single, continuous structure (e.g., a unitary structure, etc.).

According to an exemplary embodiment, the rotational stops 350 are configured to limit the amount of rotation of the pivoting carriage 310 relative to the carriage mount 320. By way of example, one of the rotational stops 350 may contact a corresponding surface (e.g., a plate, etc.) of the rear portion 120 of the chassis 100 when the pivoting carriage 310 reaches a pivoting travel limit (e.g., rotate two degrees about the longitudinal axis 330, etc.). According to an exemplary embodiment, the rotational stops 350 are sized to allow the pivoting carriage 310 to rotate about the longitudinal axis 330 to the pivoting travel limit which corresponds to a vertical displacement of at least one of the rear casters 302 of approximately plus or minus 6 millimeters (mm) (e.g., a first caster 302 displaces upward a distance and a second caster 302 displaces downward the same distance, etc.). In other embodiments, the rotational stops 350 are differently sized to allow the pivoting carriage 310 to rotate about the longitudinal axis 330 to a different pivoting travel limit (e.g., rotate one degree, rotate three degrees, etc.) which corresponds to a vertical displacement of at least one of the rear casters 302 of less than or greater than plus or minus 6 mm (e.g., 4 mm, 8 mm, etc.). In some embodiments, the rear casters 302 include a spring member to allow for additional or alternative vertical displacement to that provided by the pivoting carriage assembly 300.

In an alternative embodiment, the carriage mount 320 is laterally offset from the longitudinal axis 330 (e.g., towards one of the rear casters 302, etc.). Laterally offsetting the carriage mount 320 may facilitate vertically displacing one of the rear caster 302 a different distance than the other rear caster 302 (e.g., one may displace a first distance in one direction and the other may displace a different distance in an opposing second direction, etc.). This configuration may be advantageous if the majority of the weight supported by the surgical cart 10 is positioned towards one of the sides of the surgical cart 10. In yet another alternative embodiment, the carriage mount 320 is omitted and replaced by a central support structure configured to slidably receive a curved beam member. The curved beam member may be configured to slidably translate through the central support as the surgical cart 10 encounters various uneven surfaces causing the rear casters 302 to vertically displace. In still another alternative embodiment, the pivoting carriage assembly 300 includes a lateral plate that defines symmetrically angled slots positioned on each lateral side of the lateral plate. According to an exemplary embodiment, the symmetrically angled slots are configured to receive and engage with pins. The engagement of the pins with the symmetrically angled slots facilitates the rotation of the pivoting carriage assembly 300 about a central axis thereof defined between the symmetrically angled slots.

According to an alternative embodiment, the rotational stops 350 are omitted and the plates 316 are configured to limit an amount of rotation of the pivoting carriage 310 relative to the carriage mount 320. The rotation of the pivoting carriage 310 may be limited by an interaction between the interaction surfaces 328 of the carriage mount 320 and the plates 316. By way of example, the width of pivoting gap 318 (i.e., based on the spacing between the plates 316, the distance between the plate 316 and the interaction surface 328) may define the amount of rotation of the pivoting carriage 310 relative to the carriage mount 320 (e.g., prior to all of the load from the surgical cart 10 being transferred through a single rear caster 302, etc.). For example, the larger the width of the pivoting gap 318, a greater amount of rotation of the pivoting carriage 310 relative to the carriage mount 320 is allowed. Conversely, the smaller the width of the pivoting gap 318, a lesser amount of rotation of the pivoting carriage 310 relative to the carriage mount 320 is allowed.

Figure 12A:
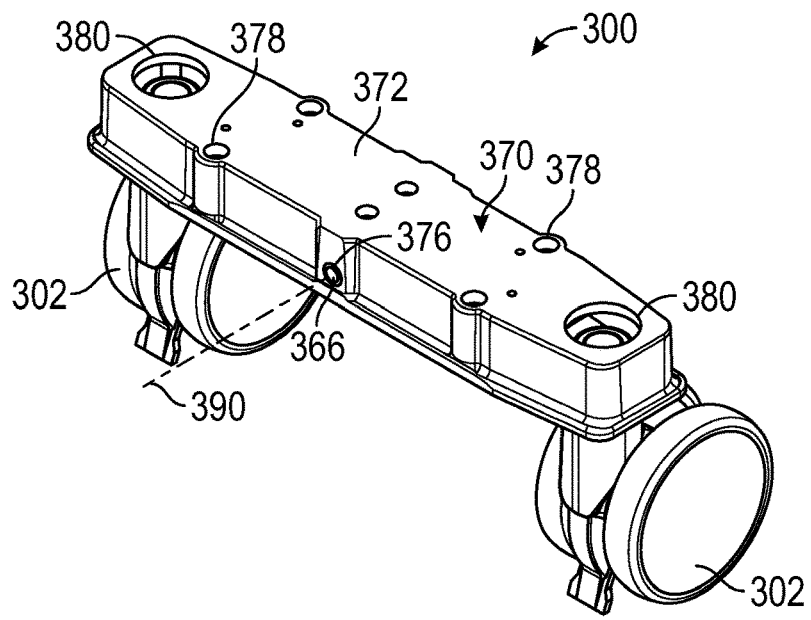
FIGS. 12A-12C are various views of a pivoting carriage assembly of the surgical cart of FIG. 10, according to an exemplary embodiment.
Figure 12B:
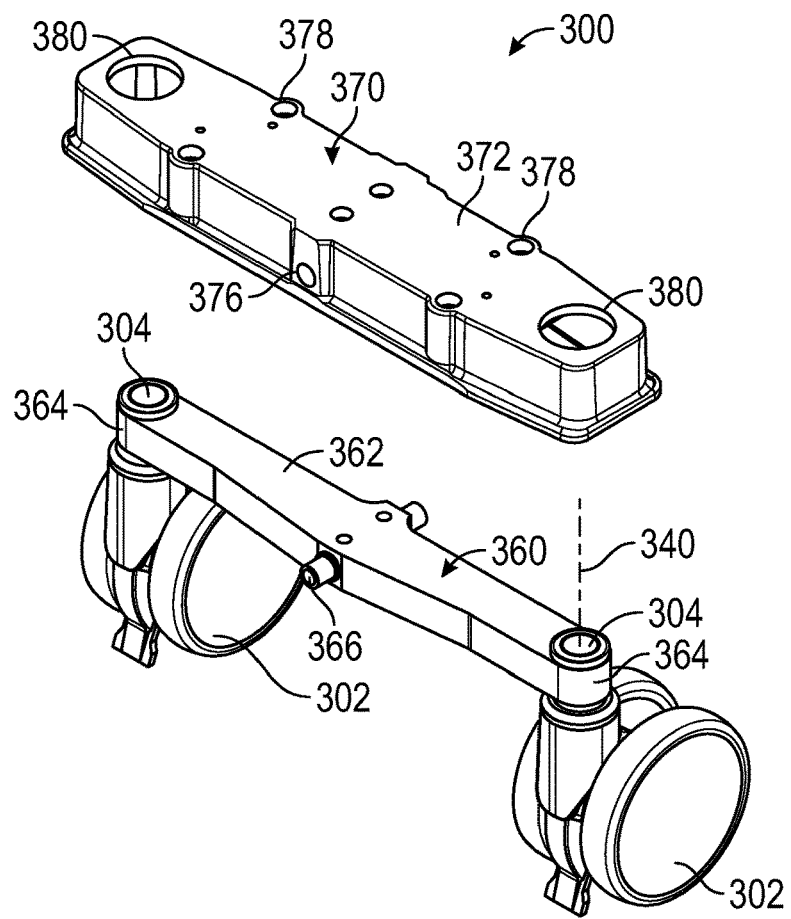

As shown in FIG. 12B, the pivoting carriage assembly 300 includes a frame member, shown as pivoting carriage 360 (e.g., a pivoting bogie, etc.). The pivoting carriage 360 includes a main portion, shown as body 362, having a pair of brackets, shown as caster brackets 364, with one positioned at each lateral end of the body 362. The caster brackets 364 are configured to couple the rear casters 302 to the pivoting carriage 360. The caster brackets 364 are configured to receive the stems 304 of the rear casters 302 to rotationally couple the rear casters 302 to the pivoting carriage 360. In an alternative embodiment, the pivoting carriage 360 defines a flat mounting location and the rear casters 302 include a corresponding flat mounting plate configured to be fastened to the flat mounting location to couple the rear casters 302 to the pivoting carriage 360. According to an exemplary embodiment, the rear casters 302 are rotationally coupled to the pivoting carriage 360 such that the rear casters 302 are free to rotate about the vertical axis 340 thereof. Thus, the rear casters 302 may freely rotate about vertical axis 340 as the surgical cart 10 is maneuvered. In some embodiments, the rear casters 302 include a brake to prevent rotation of wheels of the rear casters 302 (i.e., aid in locking the surgical cart 10 in place) and/or rotationally fix the rear casters 302 in a desired direction (i.e., prevent rotation about the vertical axis 340). In an alternative embodiment, the rear casters 302 are rotationally fixed relative to the vertical axis 340 such that they are oriented in a single direction (e.g., forward, etc.).

Figure 12C:
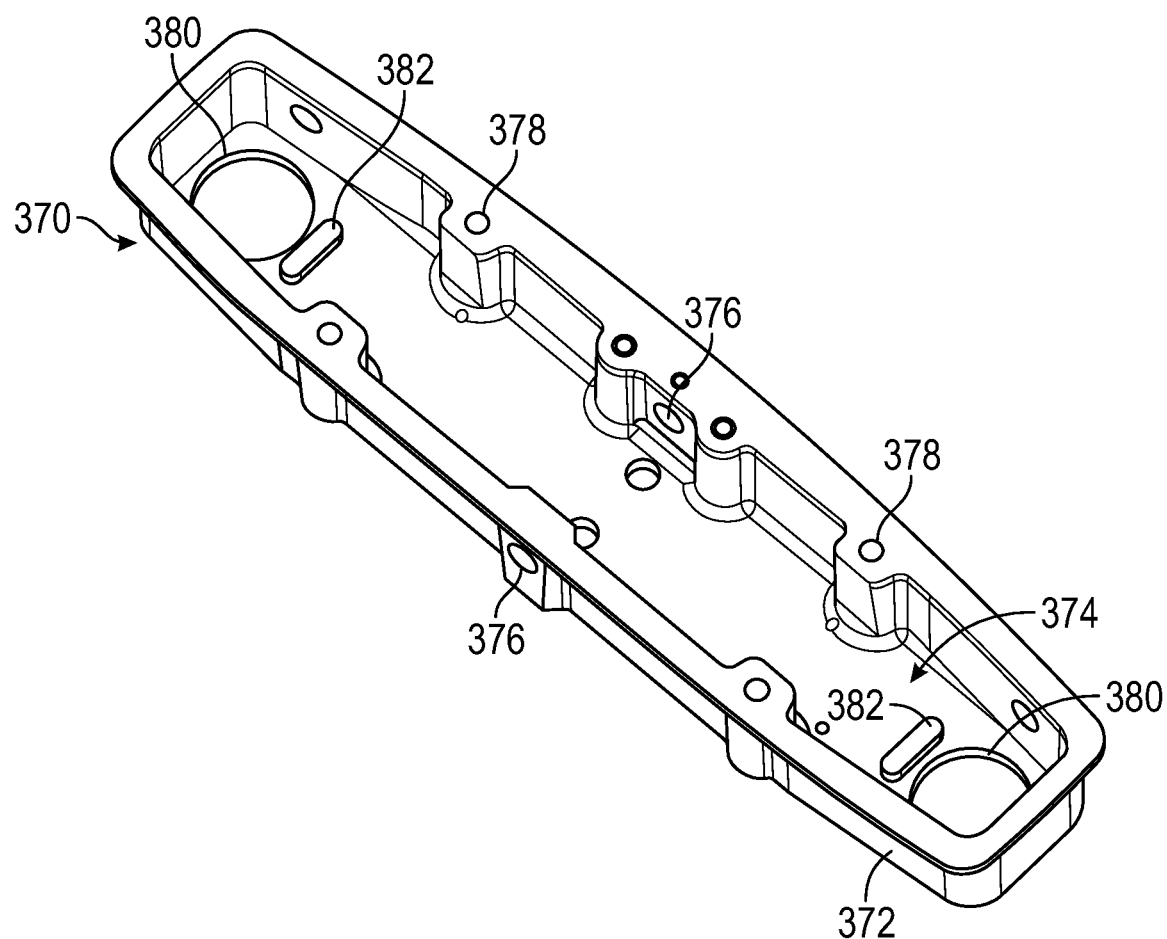

As shown in FIGS. 12A-12C, the pivoting carriage assembly 300 includes a mounting portion, shown as carriage mount 370. According to an exemplary embodiment, the carriage mount 370 is configured to pivotably couple the pivoting carriage assembly 300 to the rear portion 120 of the chassis 100. As shown in FIGS. 12A-12C, the carriage mount 370 includes a body, shown as housing 372. As shown in FIG. 12C, the housing 372 of the carriage mount 370 defines an internal cavity, shown as carriage cavity 374. According to an exemplary embodiment, the carriage cavity 374 is configured to receive the pivoting carriage 360.

As shown in FIGS. 12A-12B, the pivoting carriage 360 includes a rod, shown as pivoting rod 366, that extends from the front and rear of the body 362 of the pivoting carriage 360. As shown in FIGS. 12A-12C, the housing 372 of the carriage mount 370 defines a pair of apertures, shown as pivot apertures 376. As shown in FIG. 12A, the pivot apertures 376 are configured to receive the pivoting rod 366, thereby pivotably coupling the pivoting carriage 360 to the carriage mount 370. The interaction between the pivot apertures 376 and the pivoting rod 366 facilitates the rotation of the pivoting carriage 360 about a longitudinal axis, shown as longitudinal axis 390. In some embodiments, the rotation of the pivoting carriage 360 about the longitudinal axis 390 is aided by a lubricant and/or a bearing disposed between the pivot apertures 376 and the pivoting rod 366.

As shown in FIGS. 11 and 12A-12C, the housing 372 of the carriage mount 370 defines a plurality of apertures, shown as mounting apertures 378. As shown in FIG. 11, the mounting apertures 378 are configured to receive a plurality of fasteners (e.g., bolts, etc.), shown as fasteners 384, to thereby couple the pivoting carriage assembly 300 (e.g., the pivoting carriage 360, the carriage mount 370, etc.) to the rear portion 120 of the chassis 100.

As shown in FIG. 12C, the pivoting carriage assembly 300 includes a limiting member, shown as rotational stop 382, positioned within the carriage cavity 374 of the housing 372 (e.g., disposed along an inner surface of a top portion of the housing 372, etc.), at each longitudinal end of the carriage mount 370. In other embodiments, the pivoting carriage assembly 300 includes a different number of rotational stops 382 positioned on each lateral side of the pivoting carriage 310 (e.g., two, three, etc.). In some embodiments, the rotational stops 382 are coupled to the housing 372 (e.g., welded, glued, fastened, etc.). In some embodiments, the rotational stops 382 and the housing 372 form a single, continuous structure (e.g., a unitary structure, etc.). In an alternative embodiment, the rotational stops 382 are additionally or alternatively positioned on and/or coupled to the body 362 of the pivoting carriage 360.

According to an exemplary embodiment, the rotational stops 382 are positioned to limit the amount of rotation of the pivoting carriage 360 relative to the carriage mount 370. By way of example, one of the rotational stops 382 may contact a corresponding surface (e.g., a top surface, etc.) of the body 362 when the pivoting carriage 360 reaches a pivoting travel limit (e.g., rotates two degrees about the longitudinal axis 390, etc.). According to an exemplary embodiment, the rotational stops 382 are sized to allow the pivoting carriage 360 to rotate about the longitudinal axis 390 to the pivoting travel limit which corresponds to a vertical displacement of at least one of the rear casters 302 of approximately plus or minus 6 millimeters (mm) (e.g., a first caster 302 displaces upward a distance and a second caster 302 displaces downward the same distance, etc.). In other embodiments, the rotational stops 382 are differently sized to allow the pivoting carriage 360 to rotate about the longitudinal axis 390 to a different pivoting travel limit (e.g., rotate one degree, rotate three degrees, etc.) which corresponds to a vertical displacement of at least one of the rear casters 302 of less than or greater than plus or minus 6 mm (e.g., 4 mm, 8 mm, etc.). In some embodiments, the rear casters 302 include a spring member to allow for additional or alternative vertical displacement to that provided by the pivoting carriage assembly 300. As shown in FIGS. 12A-12C, the housing 372 of the carriage mount 370 defines an aperture, shown as aperture 380, positioned at each end of the housing 372. According to an exemplary embodiment, the apertures 380 are positioned to prevent the caster brackets 364 and/or the stems 304 from engaging the housing 372 when the pivoting carriage 360 pivots about the longitudinal axis 390 (e.g., when the pivoting travel limit is reached, etc.).

According to an exemplary embodiment, the pivoting carriage assembly 300 and the front wheels 202 provide a quasi-four-point support for the surgical cart 10 during transport and/or when stationary. For example, the pivoting ability of the pivoting carriage 310 and/or the pivoting carriage 360 configures the surgical cart 10 to function as a three-wheeled cart (e.g., all of the loading is transferred to the chassis 100 through the carriage mount 320 or the carriage mount 370, etc.) when the pivoting travel limit is not reached and into a four-wheeled cart when the pivoting travel limit is reached (e.g., the rotational stops 350 or the rotational stops 382 limit the rotation, etc.). Thus, the front wheels 202 and the pivoting carriage assembly 300 provide a deterministic three-point support for the surgical cart 10 (e.g., functions as a three-wheeled cart when the pivoting travel is not reached, etc.) for increased rocking resistance and caster fluttering resistance (e.g., relative to a traditional four-wheeled cart, etc.) and four-point support (e.g., functions as a four-wheeled cart when the pivoting travel is reached, etc.) for increased stability (e.g., improved tipping resistance, relative to a traditional three-wheeled cart, etc.).

According to an exemplary embodiment, the pivoting carriage assembly 300 facilitates the self-adjustment of the surgical cart 10 while moving and/or stationary on an uneven surface (e.g., ramps, over door sills, over cords, into an elevator, etc.) to provide the three-point support. Traditional surgical carts with four-point support may lean when encountering an uneven surface, transferring a greater amount of load to one side of the cart causing an increased risk for rocking of the cart or fluttering of a caster wheel. According to an exemplary embodiment, the rotation of the pivoting carriage 310 or the pivoting carriage 360 relative to the carriage mount 320 or the carriage mount 370, respectively, (i.e., self-adjustment) advantageously prevents rocking of the surgical cart 10. By way of example, the self-adjustment may prevent transferring all of the loading from the surgical cart 10 onto one of the rear casters 302 (e.g., the load from the surgical cart 10 is transferred to an uneven ground surface substantially through both of the rear casters 302, etc.), which effectively prevents the surgical cart 10 from rocking and/or one of the front wheels 202 and the rear casters 302 from fluttering.

Traditional surgical carts with three-point support (i.e., three-wheeled carts) may have an increased risk of tipping. According to an exemplary embodiment, the pivoting carriage assembly 300 effectively provides a four-point support when the pivoting travel limit is reached to advantageously prevent tipping of the surgical cart 10. Thus, the pivoting carriage assembly 300 eliminates rocking of the surgical cart 10 and fluttering of the front wheels 202 and the rear casters 302, while still satisfying various regulatory requirements for tipping (e.g., IEC tipping standards, etc.).

Referring now to FIGS. 2-3, 5A-5G, 10-11, and 13, the floor lock 400 is configured to stabilize the surgical cart 10 in place. The floor lock 400 is configured to prevent movement of at least one of the rear end 14 of the surgical cart 10 and the front end 12 of the surgical cart 10 in a lateral and/or a longitudinal direction when actuated (e.g., engaged with a ground surface, etc.). According to the exemplary embodiment shown in FIGS. 2-3, 5A-5G, 10-11, and 13, the floor lock 400 is a mechanical mechanism actuated by an operator of the surgical cart 10. In an alternative embodiment, the floor lock 400 is an electromechanical mechanism that is actuated by an actuator (e.g., an electric motor, etc.) in response to receiving a command from the computing system 40 (e.g., a command based on an operator input received by the display device 42 or input device 44, etc.).

According to the exemplary embodiment shown in FIGS. 5A-5F, the floor lock 400 is selectively reconfigurable between a disengaged configuration, shown as transportation configuration 402 (shown in FIGS. 5A and 5C), and an engaged, shown as machining configuration 406 (shown in FIGS. 5B and 5E) (e.g., such that the surgical cart 10 is in a machining mode, a park mode, a brake mode, etc.). The floor lock 400 may be actuated from the transportation configuration 402 to the machining configuration 406 in response to an operator of the surgical cart 10 pressing down on a pedal 412. According to an exemplary embodiment, the floor lock 400 is structured as a latching push-push mechanism that requires a single push to reconfigure the floor lock 400 from the transportation configuration 402 to the machining configuration 406 (e.g., a single push of the pedal 412 immobilizes an approximately 600 pound cart, etc.), and vice versa. Advantageously, the floor lock 400 eliminates the need for a ratcheting mechanism, a pumping mechanism, and/or an actuator (e.g., a hydraulic cylinder, an electric motor, etc.) to immobilize the surgical cart 10 with the floor lock 400 (e.g., the actuation of the floor lock 400 may be relatively easily provided by an operator of the surgical cart 10, etc.). In an alternative embodiment, the floor lock 400 is configured as a push-pull mechanism such that by pushing on the pedal 412 causes the floor lock 400 to engage a ground surface and lifting on the pedal 412 cause the floor lock 400 to disengage from the ground surface. In yet another alternative embodiment, the floor lock 400 includes a first lever configured to engage the floor lock 400 with a ground surface and a second lever configured to disengage the floor lock 400 from the ground surface.

As shown in FIGS. 5A-5F, the floor lock 400 includes a first member, shown as brake pedal 410, and a second member, shown as brake 420. The brake pedal 410 includes an actuation surface, shown as pedal 412, coupled to a pair of arms, shown as arms 414. According to an exemplary embodiment, the pedal 412 is foldable (e.g., for storage, to move out of the way, etc.). By way of example, the pedal 412 may be pivotably coupled to the arms 414 with rotational stops that facilitate selectively positioning the pedal 412 between a stowed position and an operational position. The arms 414 may define a slot configured to receive a limiter of the pedal 412. The slot may define the motion through which the limiter, and thereby the pedal 412, may travel. As shown in FIGS. 5C-5F, the arms 414 are rotationally coupled to the chassis 100 via a fastener, shown as hinge 416. As shown in FIGS. 5A-5F, the brake 420 includes an arm, shown as brake arm 422, and a pad, shown as brake pad 424, coupled to the brake arm 422. As shown in FIGS. 5C-5F, the brake arm 422 is rotationally coupled to the chassis 100 via a fastener, shown as hinge 426. As shown in FIG. 5B, the floor lock 400 includes an actuator, shown as brake actuator 430. The brake actuator 430 may include a gas cylinder, a hydraulic cylinder, a coil spring, or the like. The brake actuator 430 is configured to couple the brake pedal 410 to the brake 420.

As shown in FIGS. 5A-5F, the floor lock 400 further includes a first lever, shown as latching lever 440; a guide block, shown as cam block 450; a second lever, shown as extension lever 460; and a pair of linkages, shown as lift linkages 470. In some embodiments, the floor lock 400 includes legs (e.g., one, two, three, etc. legs), shown as front chassis legs 480, positioned at the front end 12 of the chassis 100. As shown in FIGS. 5C-5F, a first end of the latching lever 440 is pivotably coupled to the brake pedal 410 via a fastener, shown as hinge 418, and an opposing second end of the latching lever 440 is slidably coupled within a slot, shown as cam track 452, defined by the cam block 450. The opposing second end of the latching lever 440 may also be coupled to a first end of a second lever, shown as extension lever 460. An opposing second end of the extension lever 460 is coupled to a first end of the lift linkage 470. The lift linkage 470 includes a first member, shown as rotational linkage 472; a second linkage, shown as guide linkage 474; a third linkage, shown as cylinder 476; and a fourth linkage, shown as rod 478. As shown in FIGS. 5A-5F, the floor lock 400 includes a bracket, shown as bracket 479. The bracket 479 is configured to couple an opposing second end of the lift linkage 470 to the body 20 of the surgical cart 10. According to an exemplary embodiment, the lift linkage 470 is configured to facilitate lifting the front wheels 202 such that the front portion 110 of the chassis 100 kneels (i.e., a kneeling feature) until the front chassis legs 480 contact a ground surface 600. In an alternative embodiment, the lift linkage 470 is configured to facilitate the extension of the front chassis legs 480 such that the front chassis legs 480 lift the front portion 110 of the chassis 100 such that the front wheels 202 no longer engage the ground surface 600. According to an exemplary embodiment, the lift linkages 470 are or include gas springs.

Figure 5C:
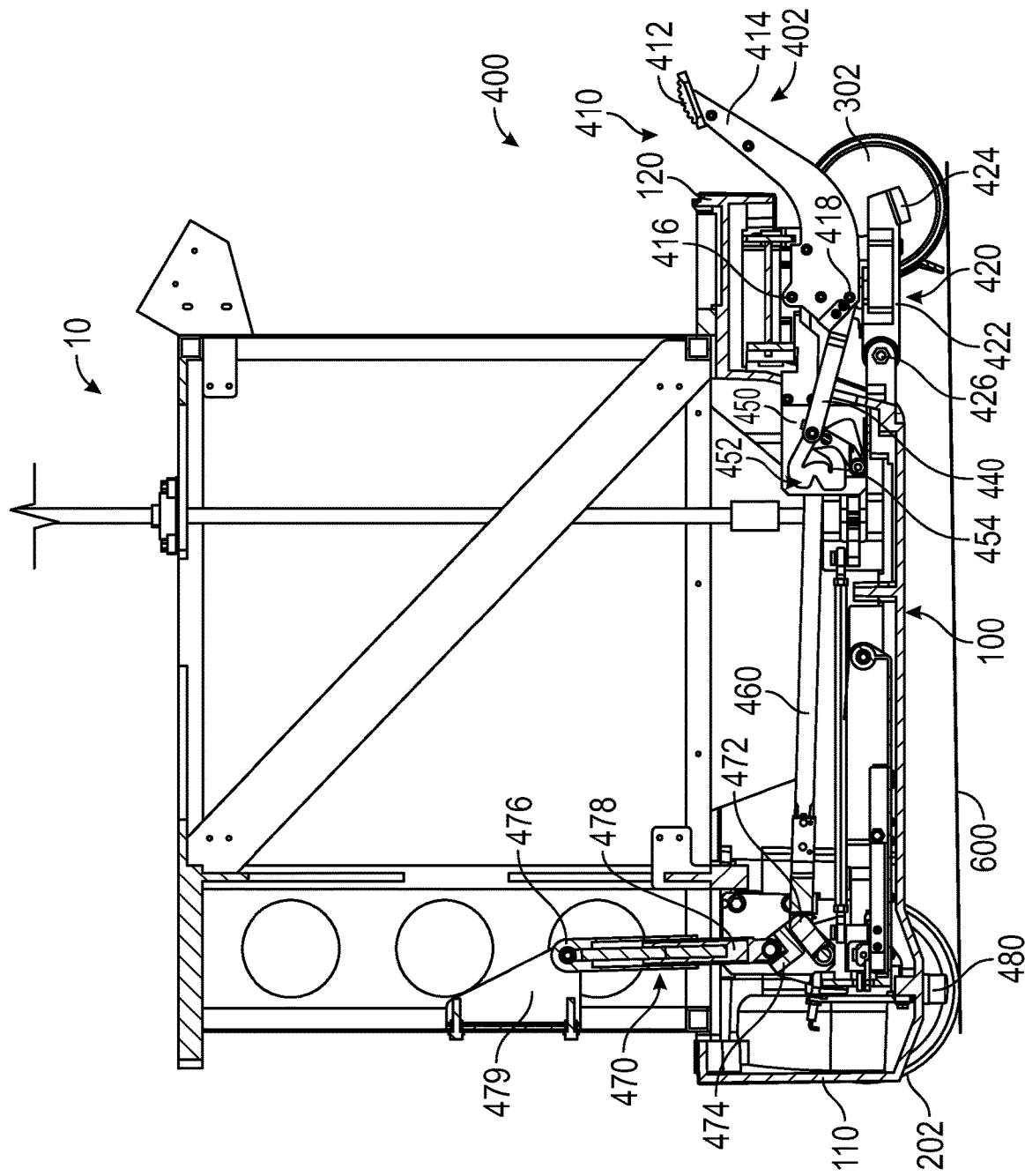
FIGS. 5C-5F are various cross-sectional views of a locking mechanism being reconfigured between a transport configuration and a braked configuration, according to an exemplary embodiment.
Figure 5D:
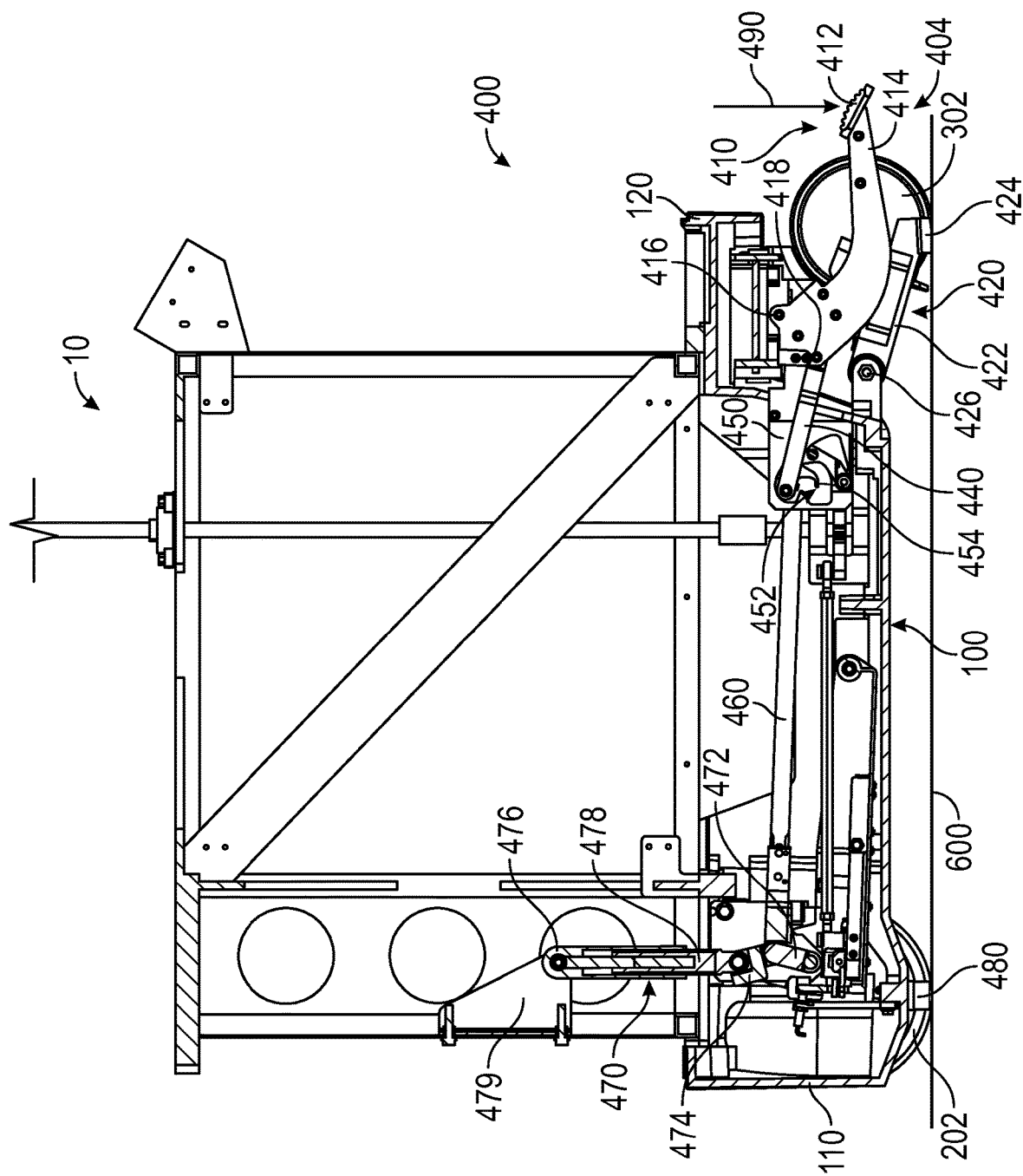

As shown in FIGS. 5A and 5C, the floor lock 400 is configured in the transportation configuration 402. The brake pad 424 and the front chassis legs 480 do not come into contact with the ground surface 600 in the transportation configuration 402, facilitating transporting and/or maneuvering the surgical cart 10 freely. As shown in FIG. 5D, a user may apply a downward actuation force on the pedal 412, indicated by directional arrow 490, such that the arms 414 rotate downward about hinge 416 and reconfigure the floor lock 400 into an intermediate configuration 404 from the transportation configuration 402. The actuation of the brake pedal 410 causes the brake arm 422 of the brake 420 to rotate about the hinge 426 (e.g., via the brake actuator 430, etc.) such that the brake pad 424 engages the ground surface 600. The actuation of the brake pedal 410 to the intermediate configuration 404 further causes the opposing second end of the latching lever 440 to follow along the cam track 452 in a first rotational direction (e.g., counter-clockwise, etc.), which thereby causes the extension lever 460 to extend and engage the rotational linkage 472 such that the rotational linkage 472 rotates. The rotation of the rotational linkage 472 causes the guide linkage 474 and the rod 478 to translate (e.g., vertically upward, etc.) such that the rod 478 slidably translates within the cylinder 476. According to an exemplary embodiment, the translation of the rod 478 corresponds with a vertical displacement of the front wheels 202 such that the front portion 110 of the chassis 100 lowers (i.e., kneels) until the front chassis legs 480 engage the ground surface 600. In an alternative embodiment, the translation of the rod 478 corresponds with a vertical displacement of the front chassis legs 480 such that the front portion 110 of the chassis 100 rises until the front wheels 202 disengage from the ground surface 600.

Figure 5E:
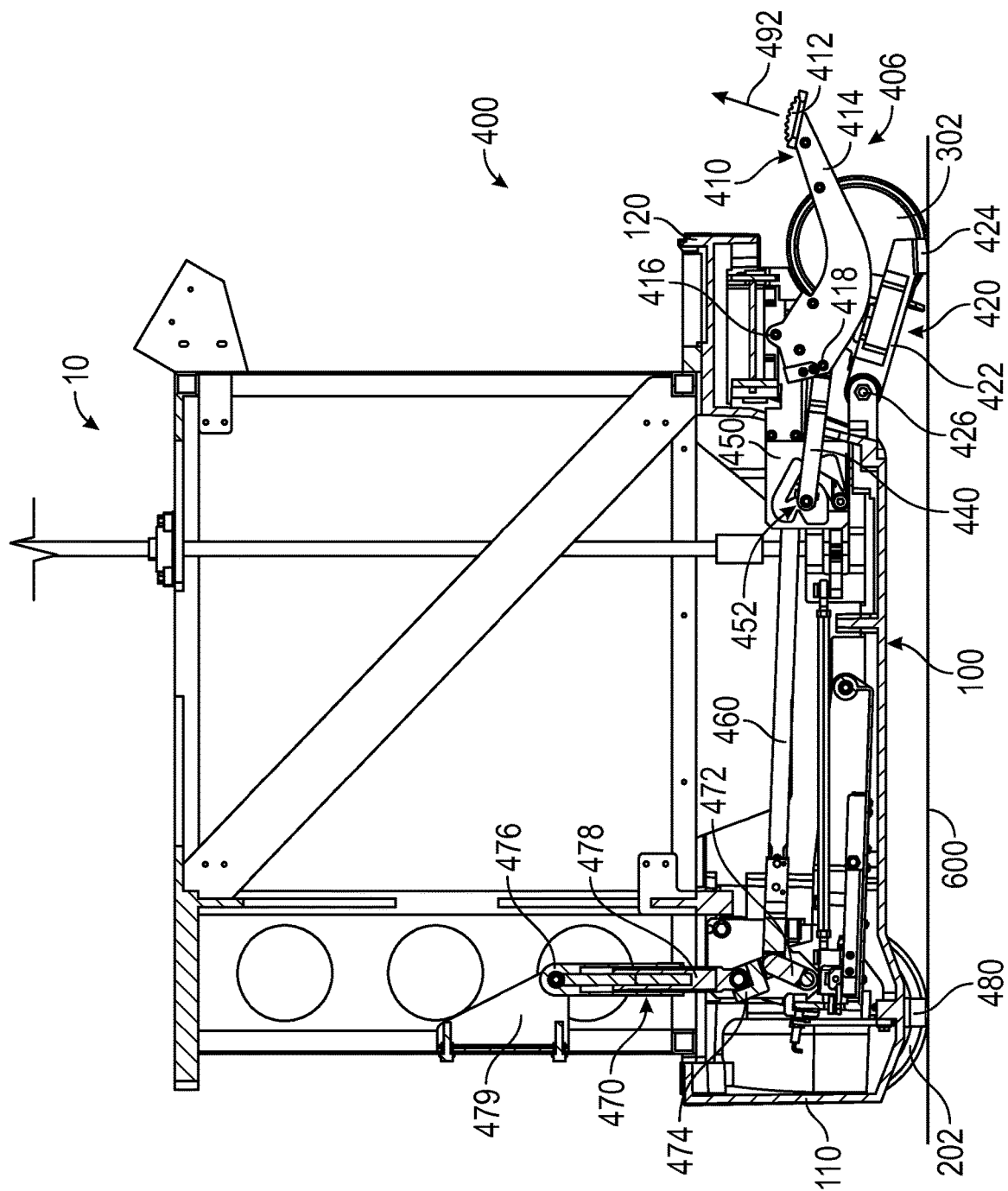

As shown in FIG. 5E, the user may stop applying the downward actuation force on the pedal 412 such that the arms 414 rotate upward about the hinge 416, as indicated by directional arrow 492, configuring the floor lock 400 into the machining configuration 406. By releasing the brake pedal 410, the latching lever 440 proceeds along the cam track 452 around a lip, shown as latching lip 454 (see, e.g., FIGS. 5C-5D). The latching lip 454 holds the latching lever 440 in place such that the floor lock 400 remains in the machining configuration 406 (e.g., without an external force being applied by an operator, etc.). It should be noted that FIGS. 5D-5E are separated for illustrative purposes only. In practice, reconfiguring the floor lock 400 of the surgical cart 10 from the transportation configuration 402 to the machining configuration 406 requires a single actuation motion (e.g., pressing down on the pedal 412 and then releasing, etc.).

Figure 5F:
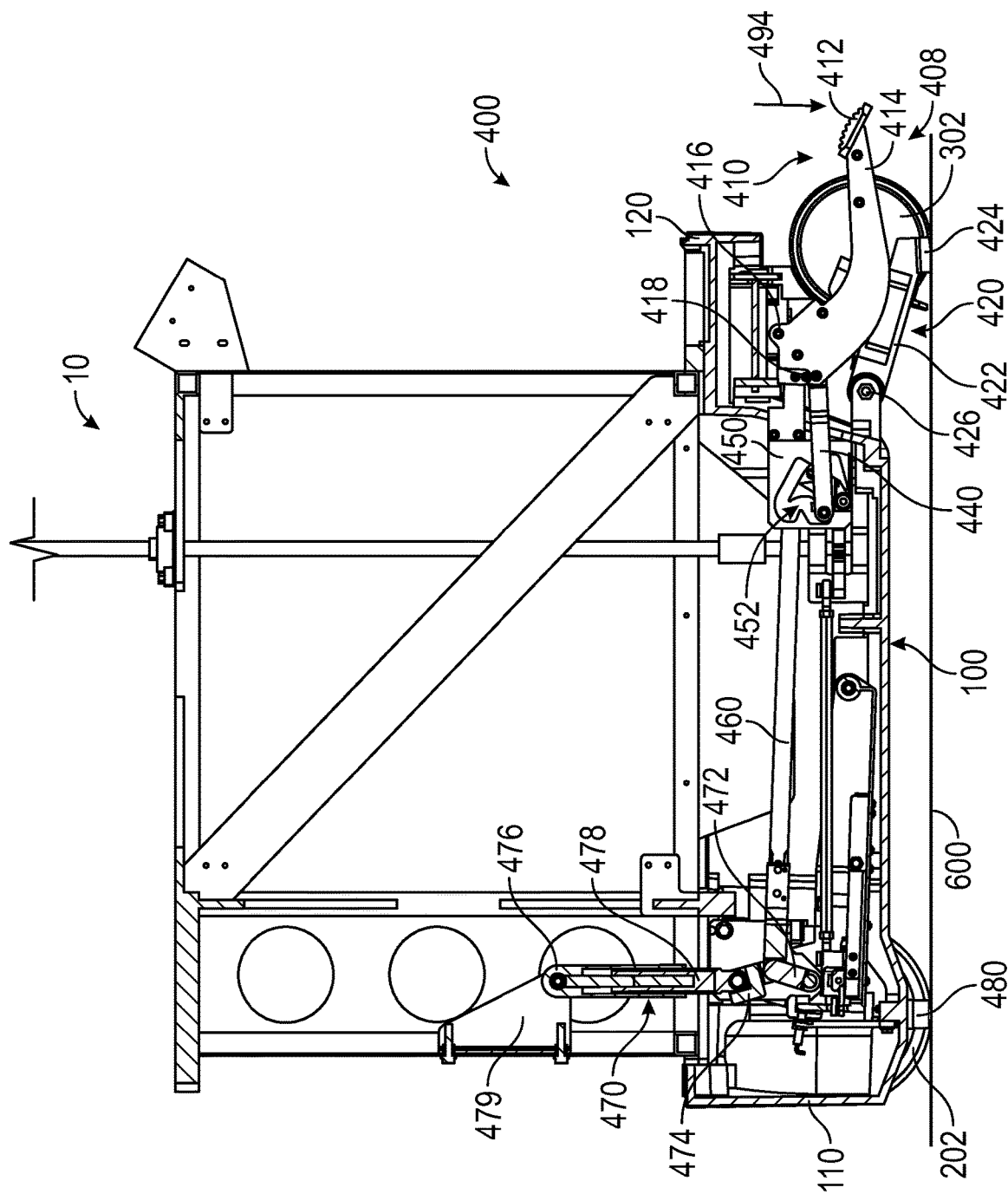

As shown in FIG. 5F, a user may apply a downward actuation force on the pedal 412, indicated by directional arrow 494, such that the arms 414 rotate downward about hinge 416 and reconfigure the floor lock 400 into a disengagement configuration 408 from the machining configuration 406. As shown in FIG. 5F, applying a downward force onto the pedal 412 when in the machining configuration 406 causes the opposing second end of the latching lever 440 to disengage from the latching lip 454. The disengagement of the opposing second end of the latching lever 440 from the latching lip 454 allows the latching lever 440 to follow along the cam track 452 in a second rotational direction (e.g., clockwise, etc.) to return the floor lock to the transportation configuration 402. For example, following the application of the downward force, a user may remove the force from the pedal 412 (e.g., release the pedal 412, etc.) such that the latching lever 440 moves in the second rotational direction around the cam track 452. Thus, the brake pedal 410 rotates about the hinge 416 and returns to the position shown in FIG. 5C (i.e., the transportation configuration 402), thereby causing the brake 420 to rotate about the hinge 426 such that the brake pad 424 disengages from the ground surface 600. Further, the extension lever 460 retracts, thereby causing the guide linkage 474 and the rod 478 to translate vertically downward such that the rod 478 slidably translates out from the cylinder 476. In turn, the front wheels 202 extend downward to engage the ground surface 600, lifting the front portion 110 of the chassis such that the front chassis legs 480 disengage from the ground surface 600.

Figure 13:
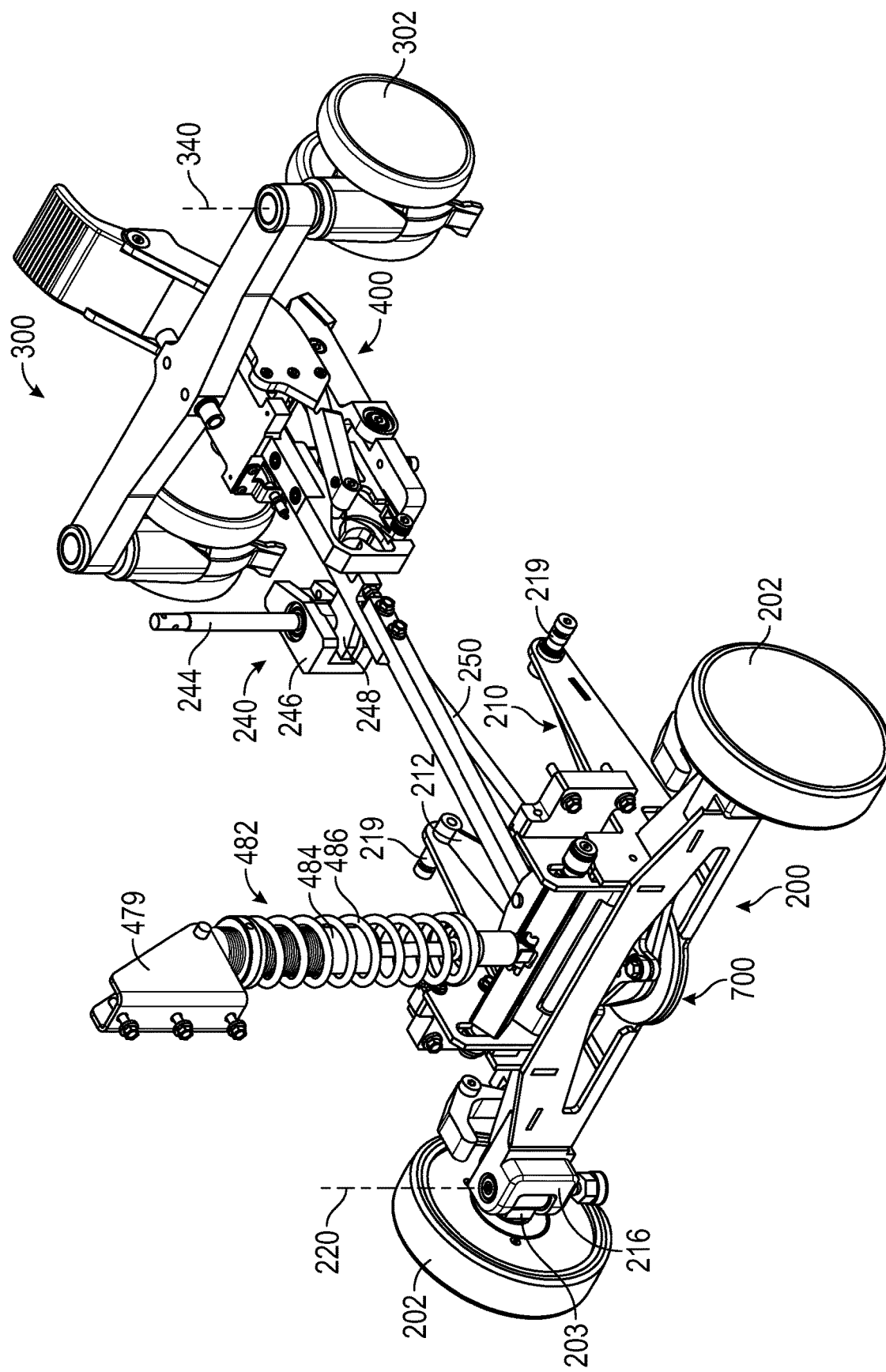
FIGS. 13-14B are various perspective views of a steering assembly of the surgical cart of FIG. 10, according to an exemplary embodiment.

As shown in FIGS. 11 and 13, the lift linkages 470 (e.g., the cylinder 476 and the rod 478, etc.) may be replaced with a suspension element, shown as coilover 482. The coilover 482 includes a shock absorber, shown as shock 484, and a resilient member, shown as coil spring 486, encircling the shock 484. According to an exemplary embodiment, the coilover 482 is configured to provide controlled dampening as the front portion 110 of the chassis 100 kneels and lifts. In other embodiments, the floor lock 400 includes a plurality of coilovers 482 (e.g., two, three, etc.).

According to an exemplary embodiment, the engagement of the brake pad 424 with the ground surface 600 substantially prevents movement of the rear end 14 of the surgical cart 10 (e.g., in a lateral and a longitudinal direction, etc.) and the engagement of the front chassis legs 480 with the ground surface 600 substantially prevents movement of the front end 12 of the surgical cart 10 (e.g., in a lateral and a longitudinal direction, etc.), thereby establishing complete immobility of the surgical cart 10 (e.g., without locking the rear casters 302 and/or the front wheels 202, etc.). In some embodiments, the brake pad 424 and/or the front chassis legs 480 include a resilient material (e.g., rubber, etc.) to at least one of (i) increase the friction between the brake pad 424 and/or the front chassis legs 480 and the ground surface 600 and (ii) attenuate loads transferred from the surgical cart 10 to the ground surface 600 (e.g., increasing the stability of the surgical cart 10, increasing the accuracy of the surgical device 30, etc.). According to an exemplary embodiment, the floor lock 400 does not lift the rear casters 302 of the surgical cart 10 off of the ground surface 600. This may advantageously reduce the amount of force required to engage the floor lock 400 with the ground surface 600 to immobilize the surgical cart 10 (e.g., as compared to lifting the rear end 14 of the surgical cart 10 off of the ground surface 600 with the floor lock 400, etc.). The floor lock 400 applies force to the ground surface via the brake pad 424 thereby preventing movement of the rear end 14 of the surgical cart 10. According to an exemplary embodiment, the front wheels 202 retract and/or the front chassis legs 480 extend such that the front wheels 202 no longer touch the ground surface 600 when the front chassis legs 480 engage the ground surface 600 (e.g., free to rotate, completely unloaded, etc.).

Figure 5G:
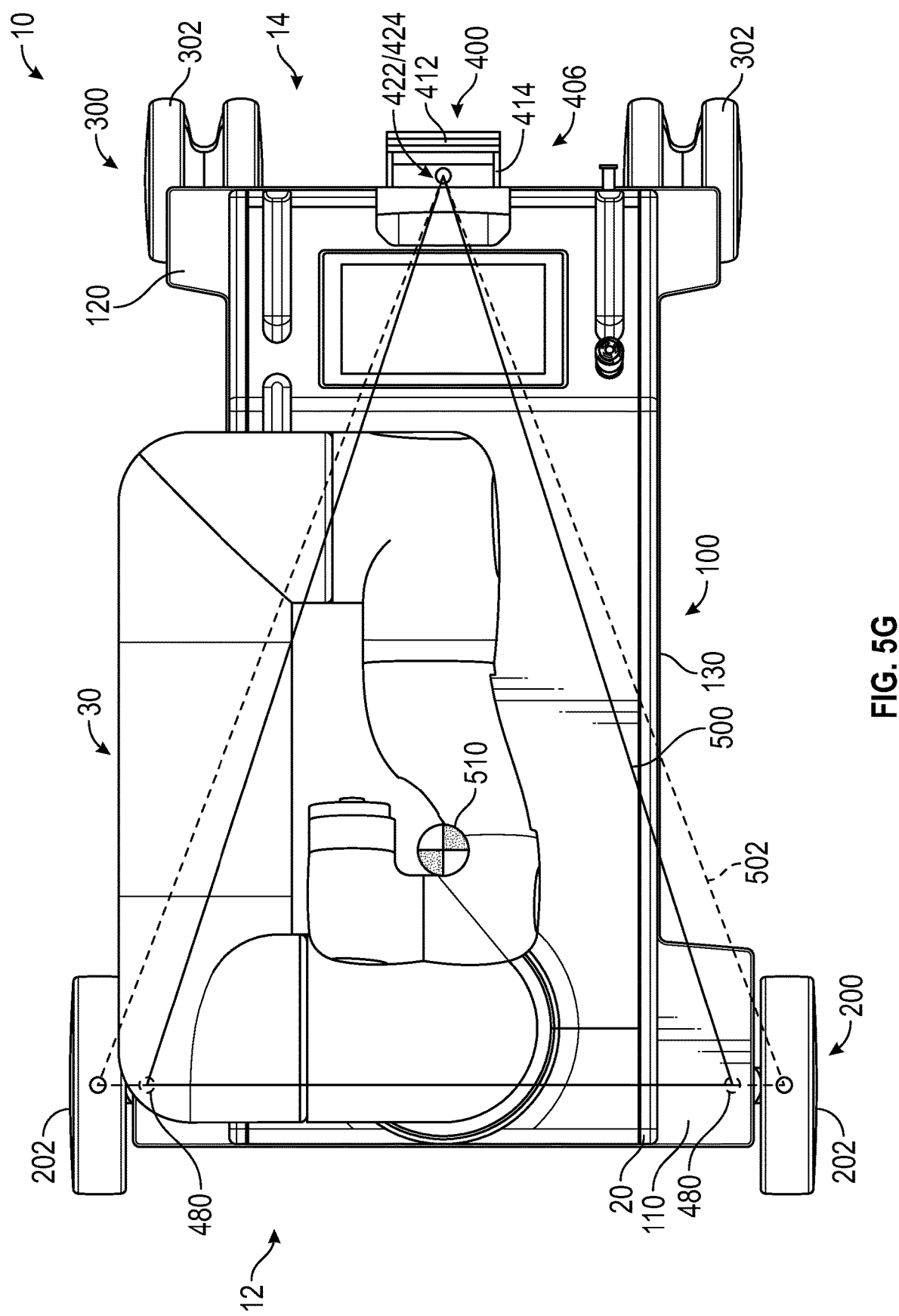
FIG. 5G is a top plan view of the surgical cart of FIGS. 1-3 with a locking mechanism in a braked configuration, according to an exemplary embodiment.

Referring now to FIG. 5G, the floor lock 400, the carriage mount 320, and/or the carriage mount 370, along with the front chassis legs 480, provide a three-point support structure 500 for the surgical cart 10 when the floor lock 400 is in the machining configuration 406. Optimum stability of the surgical cart 10 during use of the surgical device 30 (e.g., when the surgical device 30 is moving, used in a procedure, machining, etc.) is achieved when the mass of the surgical cart 10 is kinematically supported by three points and the center of the mass is located at the approximate centroid of an area defined by the three points. According to an exemplary embodiment, the surgical cart 10 is supported by the three-point support structure 500 which includes each of the front chassis legs 480, the carriage mount 320, the carriage mount 370, and/or the brake pad 424 of the brake 420. Also, a center of mass 510 of the surgical cart 10 is substantially near the centroid of the area defined by the three-point support structure 500. Therefore, the surgical cart 10 has three point stability when the floor lock 400 is in the machining configuration 406 (i.e., increased stability when stationary for machining) and quasi-four point stability (e.g., from the front wheels 202 and the pivoting carriage assembly 300, etc.) when the floor lock 400 is in the transportation configuration 402 (i.e., increased stability when moving, prevents rocking, fluttering, and tipping during transport). According to an exemplary embodiment, the chassis 100 is relatively stiff to minimize deflection as loads are transferred through the surgical cart 10 from the surgical device 30 during operation (e.g., machining, etc.), further increasing the accuracy of the surgical device 30.

In an alternative embodiment, the extension lever 460, the lift linkages 470, the coilover 482, and/or the front chassis legs 480 are omitted. In the alternative embodiment, the carriage mount 320, the carriage mount 370, and/or the floor lock 400, along with the front wheels 202, provide a three-point support structure 502 for the surgical cart 10 when the floor lock 400 is in the machining configuration 406 (e.g., without raising or lowering any portion of the surgical cart 10, the front portion 110 of the chassis 100 may not kneel, etc.). Engaging the floor lock 400 may (i) lock the front wheels 202 in the current position thereof or (ii) pivot and/or lock the front wheels 202 into a desired positon (e.g., a fore-and-aft positon, a lateral position, etc.). In one embodiment, actuating the floor lock 400 orients and/or locks the front wheels 202 in a longitudinal direction (i.e., forward). Longitudinally disposing the front wheels 202 (as shown in FIGS. 5A-5B) may prevent lateral movement of the front end 12, thereby establishing complete immobility of the surgical cart 10. In another embodiment, actuating the floor lock 400 orients and/or locks the front wheels 202 in a lateral direction (i.e., sideways). Laterally disposing the front wheels 202 may further prevent longitudinal movement of the front end 12 of the surgical cart 10. In other embodiments, engaging the floor lock 400 neither locks the front wheels 202 nor orients the front wheels 202 into a desired position (e.g., the front wheels 202 may be manually pivoted into a desired positon, the front wheels 202 may be manually locked, etc.). In some embodiments, the front wheels 202 include a brake mechanism positioned to rotationally fix the front wheels 202. In yet another alternative embodiment, the surgical cart 10 includes one or more floor locks 400 positioned at the front end 12 of the surgical cart 10 to immobilize the front end 12 of the surgical cart 10. In a further alternative embodiment, the chassis 100 includes one or more rear chassis legs such that the surgical cart 10 is able to be lowered onto the rear chassis legs (e.g., such that the front chassis legs 480 and the rear chassis leg(s) immobilize the surgical cart 10, the front wheels 202 and the rear chassis leg(s) immobilize the surgical cart 10, etc.).

Referring now to FIGS. 5A-5B, 6-9B, 11, and 13-17B, the wheel steering assembly 200 is configured to facilitate maneuvering the surgical cart 10 in a plurality of steering modes (e.g., fore-and-aft, turn-on-axis, lateral, etc.). As shown in FIGS. 5A-5B, 6, 7A, 8A, 9A, 11, 13-14B, 15B, 16B, and 17B, the wheel steering assembly 200 includes a steering frame member, shown as steering swing arm 210. As shown in FIGS. 6-7A, 8A, 9A, 11, 13-14B, 15B, 16B, and 17B, the steering swing arm 210 includes a plate, shown as steering plate 212; a wall, shown as wall 214, that extends around a periphery of the steering plate 212; and a pair of brackets, shown as wheel brackets 216, coupled to the wall 214. The wheel brackets 216 are configured to couple the front wheels 202 to the steering swing arm 210. As shown in FIG. 7B, the front portion 110 of the chassis 100 defines apertures, shown as wheel apertures 116, positioned such that the wheel brackets 216 extended from the wheel apertures 116. Thus, the front wheels 202 are able to be positioned outside of the chassis 100.

As shown in FIGS. 6-7A, 8A, and 9A, the steering swing arm 210 includes a pair of mounts, shown as steering assembly mounts 218. As shown in FIGS. 5A-5B, the steering assembly mounts 218 are configured to couple the wheel steering assembly 200 to the chassis 100 within the inner volume 112. According to an exemplary embodiment, the middle portion 130 of the chassis 100 defines a set of apertures that correspond with apertures defined by the steering assembly mounts 218. The corresponding apertures receive fasteners (e.g., nuts and bolts, etc.) which removably couples the steering swing arm 210 to the chassis 100. According to an exemplary embodiment, the steering assembly mounts 218 pivotably couple the steering swing arm 210 to the chassis 100 which thereby facilitates the rotation of the steering swing arm 210 as the front portion 110 of the chassis 100 kneels (e.g., when the floor lock 400 is engaged, etc.).

As shown in FIGS. 11, 13-14B, 15B, 16B, and 17B, the steering swing arm 210 includes a pair of pivots, shown as steering assembly pivots 219, extending laterally therefrom. As shown in FIG. 11, the middle portion 130 of the chassis 100 defines a pair of mounts, shown as couplers 132, that are positioned to receive the steering assembly pivots 219. The steering assembly pivots 219 are thereby configured to couple the wheel steering assembly 200 to the chassis 100 within the inner volume 112. According to an exemplary embodiment, the steering assembly pivots 219 pivotably couple the steering swing arm 210 to the chassis 100 which thereby facilitates the rotation of the steering swing arm 210 as the front portion 110 of the chassis 100 kneels (e.g., when the floor lock 400 is engaged, etc.).

As shown in FIGS. 6-7A, 8A, 9A, 11, and 13, the wheel steering assembly 200 includes a steering mechanism, shown as steering mechanism 240. According to an exemplary embodiment, the steering mechanism 240 is configured as a manually actuated mechanical linkage and/or crank system that steers the front wheels 202 in response to a manual actuation from an operator of the surgical cart 10. According to an exemplary embodiment, the mechanical linkage and/or crank system of the steering mechanism 240 eliminates the need for belts, gears, sprockets, and/or adjustments, thereby reducing costs and minimizing maintenance. In an alternative embodiment, the steering mechanism 240 is an electromechanical linkage system that is actuated by an actuator (e.g., an electric motor, etc.) in response to receiving an command from the computing system 40 (e.g., a command based on an operator input received by the display device 42 or input device 44, etc.). In another alternative embodiment, each of the front wheels 202 and/or rear casters 302 include an actuator (e.g., an electric motor, etc.) positioned to steer each of the front wheels 202 and the rear casters 302 independently in response to receiving a command from the computing system 40. In some embodiments, an electric motor is adapted to propel the surgical cart 10 by providing rotational energy to at least one of the front wheels 202 and the rear casters 302.

Figure 6:
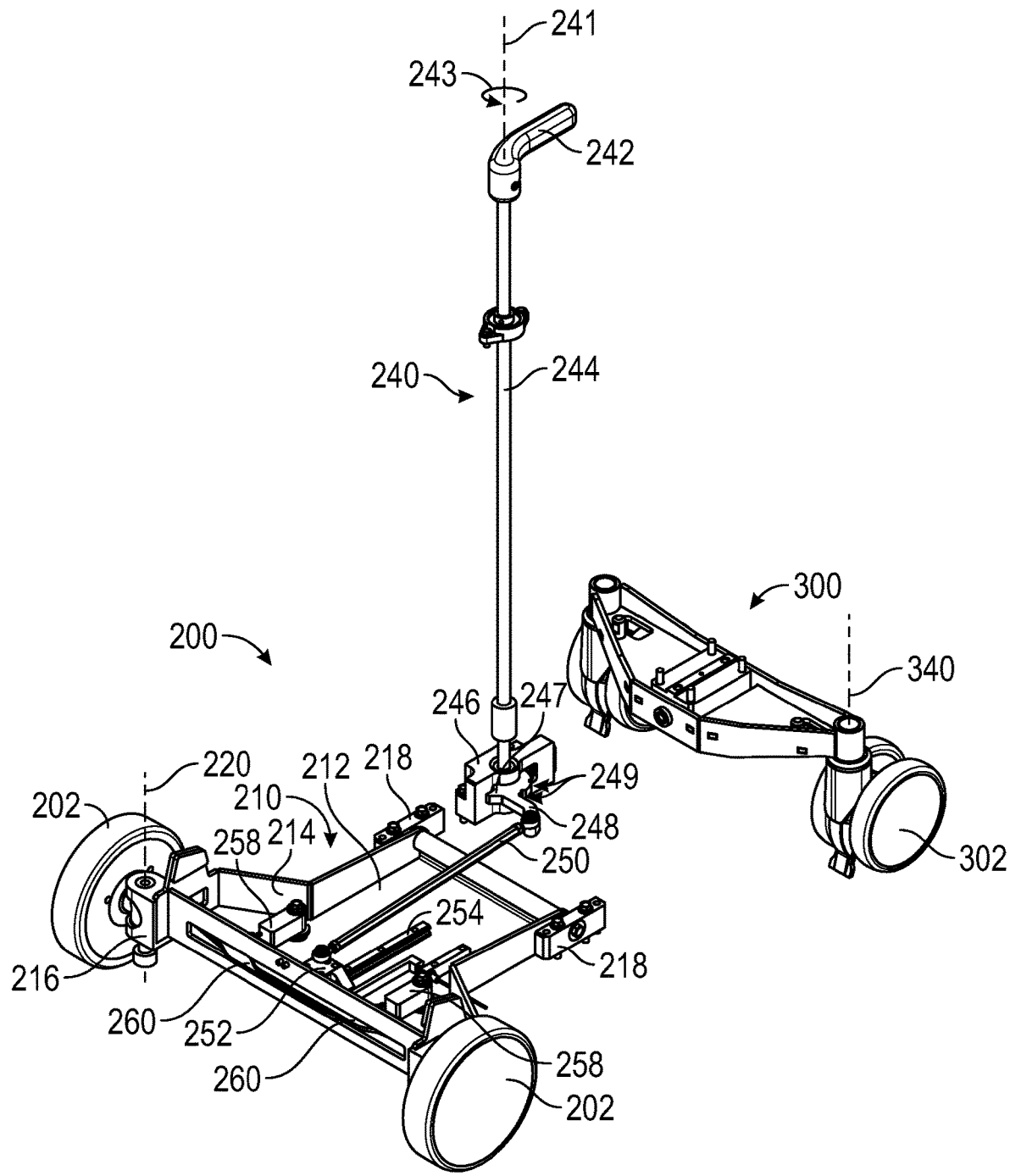
FIG. 6 is a perspective view of a steering assembly of the surgical cart of FIG. 1, according to an exemplary embodiment.

As shown in FIGS. 5A-5B, 6-7A, 8A, and 9A, the steering mechanism 240 includes a handle 242. The handle 242 is configured to provide an operator of the surgical cart 10 with a lever to apply leverage in order to reconfigure the steering mechanism 240 into the plurality of steering modes. As shown in FIGS. 5A-5B and 6, the handle 242 is coupled to a shaft 244 which defines an axis, shown as rotational axis 241. By way of example, turning handle 242 about rotational axis 241 as indicated by directional arrow 243 may reconfigure the steering mechanism 240 into a desired steering mode.

As shown in FIGS. 5A-5B, 6, and 13, the shaft 244 extends from the handle 242 to an indexing member, shown as indexing case 246. In other embodiments, the shaft 244 extends from one of the handgrips 52 to the indexing case 246. As shown in FIGS. 5A-5B, the indexing case 246 is coupled to the chassis 100 (e.g., via a fastener, etc.). As shown in FIGS. 6-7A, 8A, 9A, and 13, the indexing case 246 include a first linkage member, shown as rotational linkage 248, rotationally coupled to the shaft 244 and disposed within the indexing case 246. The rotational linkage 248 includes an extension, shown as retaining leg 247. The retaining leg 247 is configured to abut the indexing case 246 to limit the rotation of the rotational linkage 248 in a first direction (e.g., clockwise, etc.) while allowing rotation of the rotational linkage 248 in an opposing second direction (e.g., counterclockwise, etc.). The rotational linkage 248 also defines a plurality of indentations, shown as indicator indentations 249. Each indicator indentation 249 may correspond with an orientation of the handle 242 that is associated with a steering mode of the surgical cart 10. For example, a first indicator indentation 249 may be associated with a fore-and-aft steering mode, a second indicator indentation 249 may be associated with a turn-on-axis steering mode, and a third indicator indentation 249 may be associated with a lateral steering mode. According to an exemplary embodiment, as the rotational linkage 248 rotates, the indicator indentations 249 interact with a movable member (e.g., an indexer, a spring-loaded ball bearing, etc.) positioned within the indexing case 246 to provide an operator with feedback (e.g., tactile feedback, etc.) that a preset steering mode is engaged. The indicator indentations 249 may also facilitate holding the steering mechanism 240 in a desired one of the preset steering modes (e.g., via the interaction between the indicator indentation 249 and the moveable member, etc.).

Figure 7A:
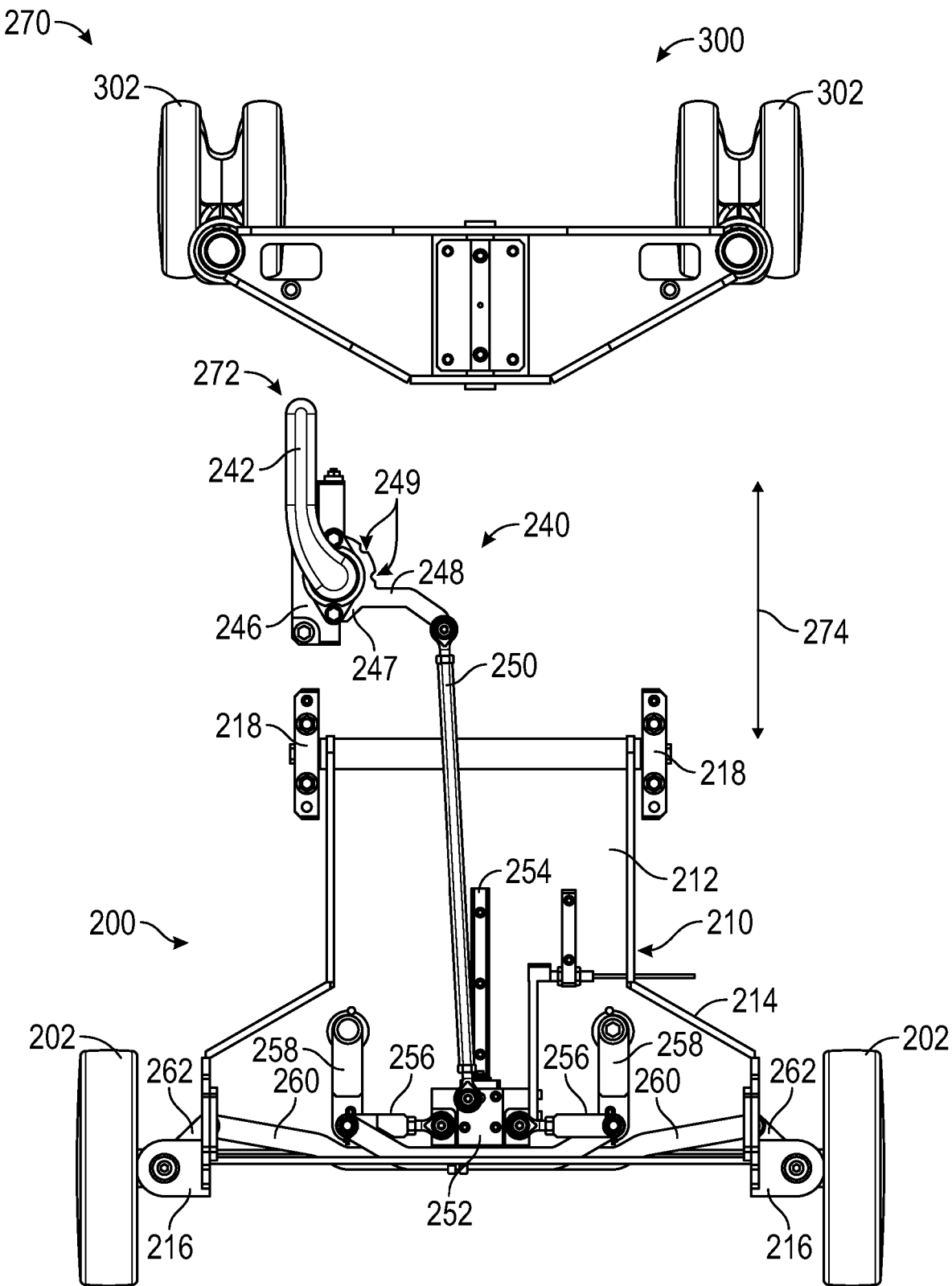
FIGS. 7A-7B are various views of the steering assembly of the surgical cart of FIG. 6 in a first configuration, according to an exemplary embodiment.
Figure 7B:
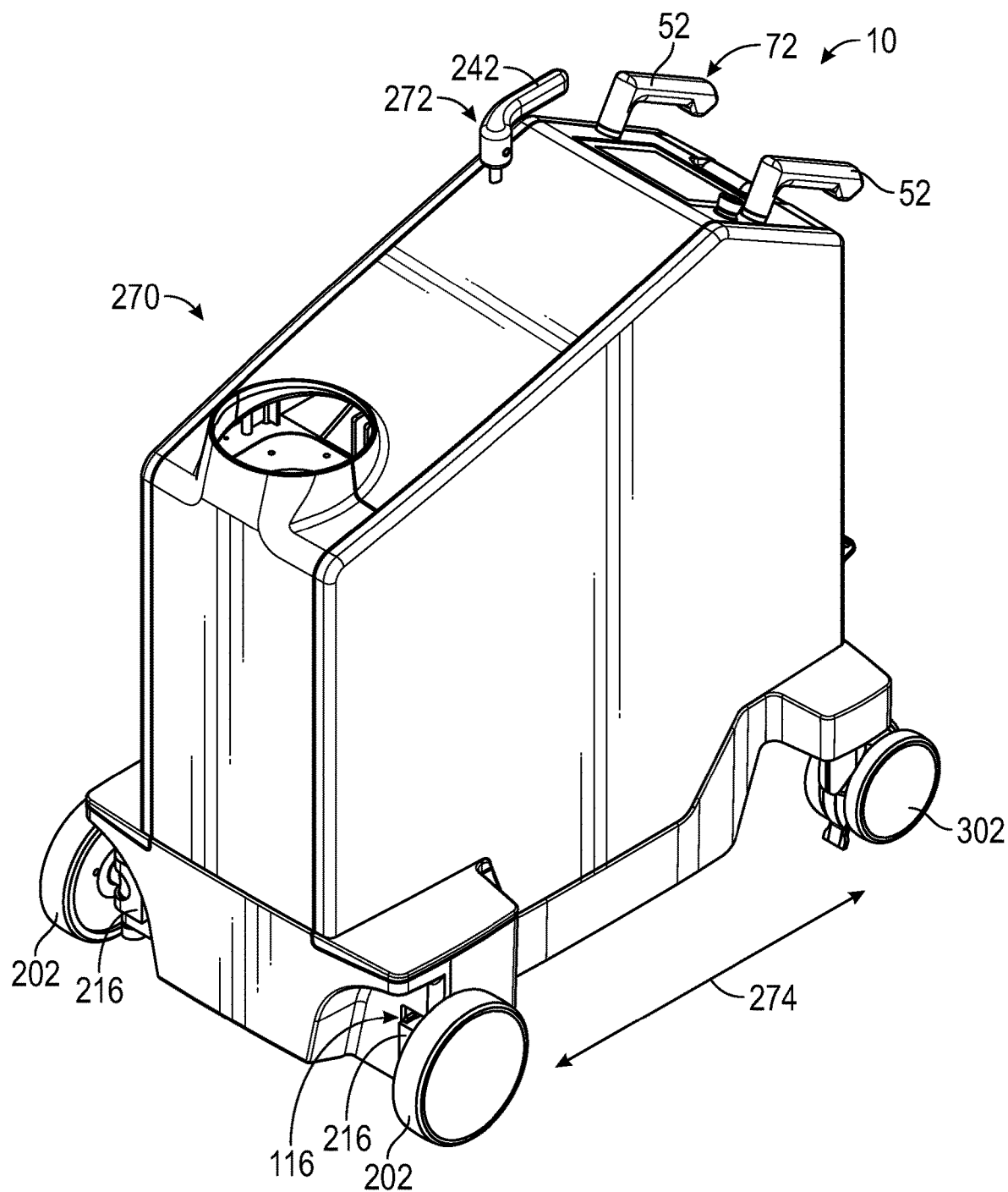
Figure 8A:
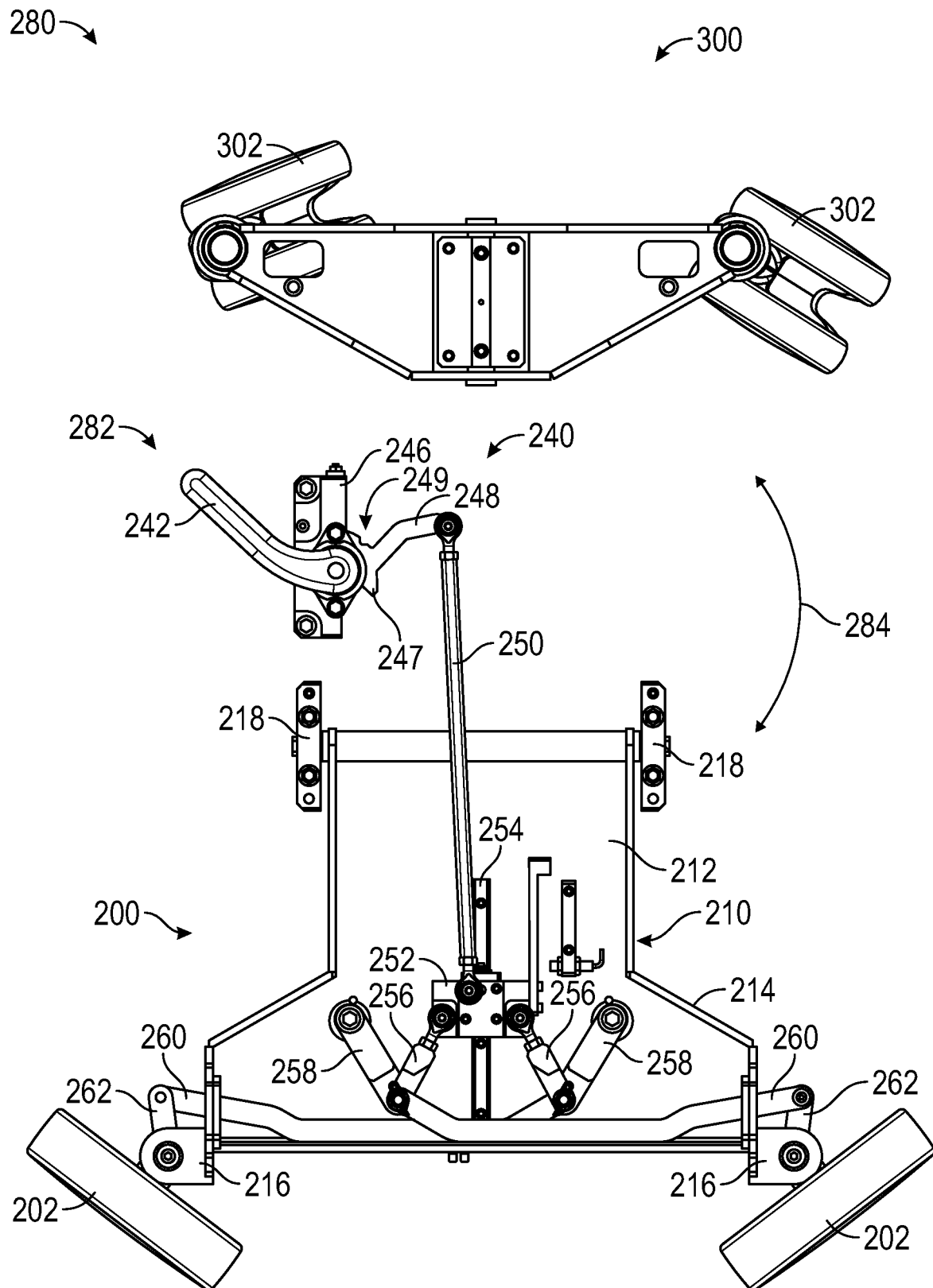
FIGS. 8A-8B are various views of the steering assembly of the surgical cart of FIG. 6 in a second configuration, according to an exemplary embodiment.
Figure 9A:
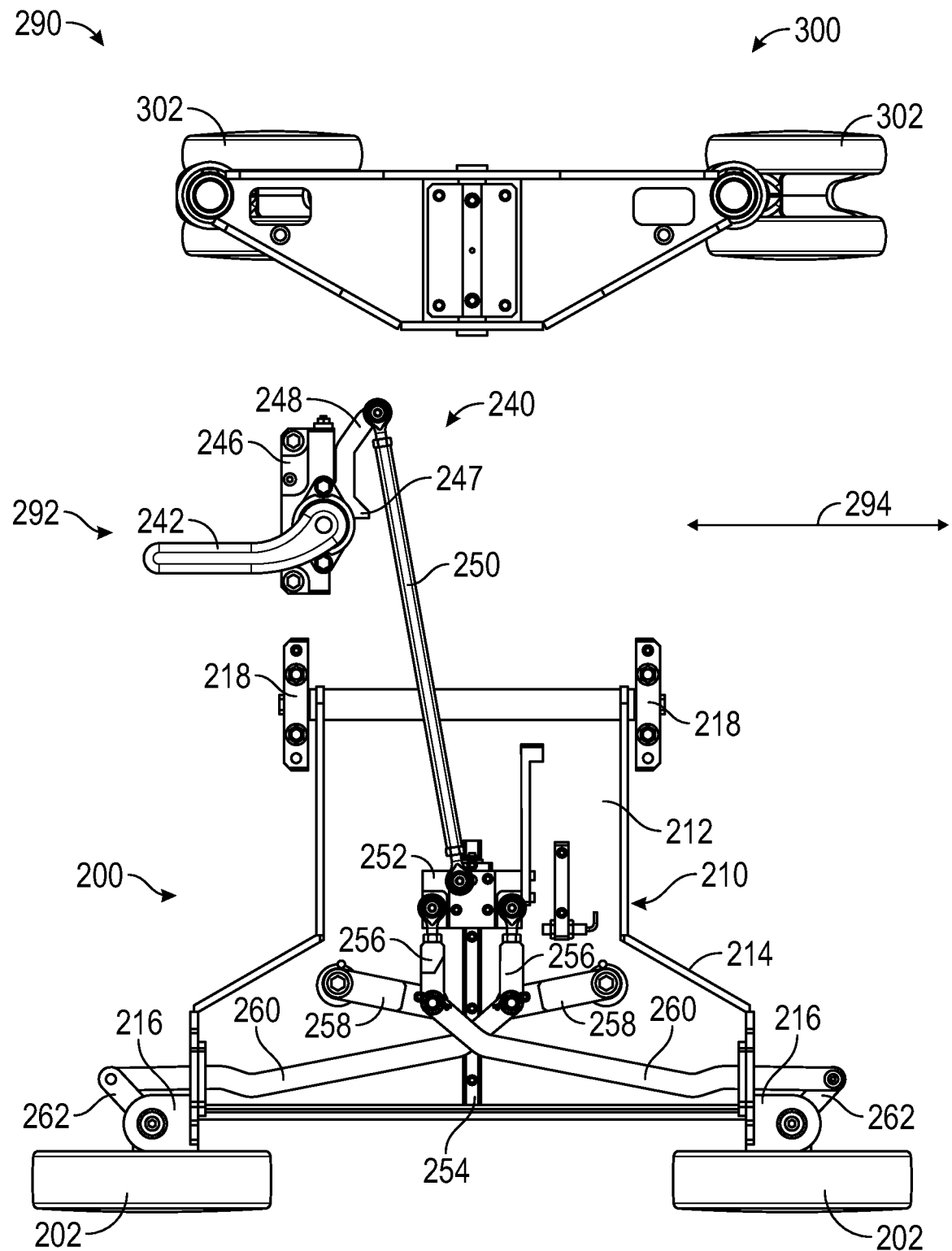
FIGS. 9A-9B are various views of the steering assembly of the surgical cart of FIG. 6 in a third configuration, according to an exemplary embodiment.

As shown in FIGS. 6-7A, 8A, 9A, and 13, the rotational linkage 248 is coupled to a first end of a second linkage member, shown as connecting linkage 250. As shown in FIGS. 6-7A, 8A, and 9A, an opposing second end of the connecting linkage 250 is coupled to a transfer member, shown as transfer block 252. The connecting linkage 250 is configured to transfer the rotational input provided by the rotational linkage 248 from the handle 242 to the transfer block 252. As shown in FIGS. 7A, 8A, and 9A, the transfer block 252 is coupled to a first end of a pair of third linkages, shown as intermediate linkages 256. Thus, the transfer block 252 couples the connecting linkage 250 to the intermediate linkages 256. As shown in FIGS. 6-7A, 8A, and 9A, the transfer block 252 is slidably coupled to a slide member, shown as linear slide 254. Thus, the transfer block 252 converts the rotational input from the handle 242 to a linear translation along the linear slide 254.

As shown in FIGS. 7A, 8A, and 9A, an opposing second end of each of the intermediate linkages 256 is coupled to a first end of a fourth linkage, shown as rotational linkage 258, and a first end of a fifth linkage, shown as driving linkage 260. As shown in FIGS. 6-7A, 8A, and 9A, an opposing second end of the rotational linkages 258 is rotationally coupled to the steering plate 212. Thus, rotational linkages 258 rotate about a point of connection between the opposing second end of the rotational linkages 258 and the steering plate 212. As shown in FIGS. 7A, 8A, and 9A, as the transfer block 252 is repositioned along the linear slide 254 (e.g., by actuating the handle 242, etc.), the intermediate linkages 256 both rotate and translate, while the rotational linkages 258 only rotate. Therefore, the movement of the intermediate linkages 256 is defined by the linear movement of the transfer block 252 and the rotational movement of the rotational linkages 258.

As shown in FIGS. 7A, 8A, and 9A, an opposing second end of the driving linkages 260 is coupled to a first end of a sixth linkage, shown as wheel linkage 262. An opposing second end of the wheel linkages 262 is coupled to the front wheels 202. As the handle 242 is actuated, the driving linkages 260 both rotate and translate causing the opposing second end of the driving linkages 260 to extend through the wheel apertures 116. The extension outwards from the wheel apertures 116 cause the wheel linkages 262 to rotate about a vertical axis, shown as wheel axis 220 (shown in FIG. 6). Accordingly, the rotation of the wheel linkages 262 causes the front wheels 202 to rotate about the wheel axis 220.

As shown in FIGS. 13-14B, 15B, 16B, and 17B, the opposing second end of the connecting linkage 250 is coupled to a crank mechanism, shown as crank mechanism 700. As shown in FIGS. 14A-14B, 15B, 16B, and 17B, the crank mechanism 700 includes a rotational synchronization element, shown as cam 710, a rotational element, shown as rotor 720, a pair of linkages, shown as arms 730, and a pair of pivoting joints, shown as wheel joints 740. According to an exemplary embodiment, the rotor 720 is rotationally coupled to the steering plate 212 (e.g., with a rotational bearing, etc.) of the steering swing arm 210. The cam 710 is rotationally fixed to the rotor 720 such that the cam 710 rotates therewith, according to an exemplary embodiment.

Figure 14A:
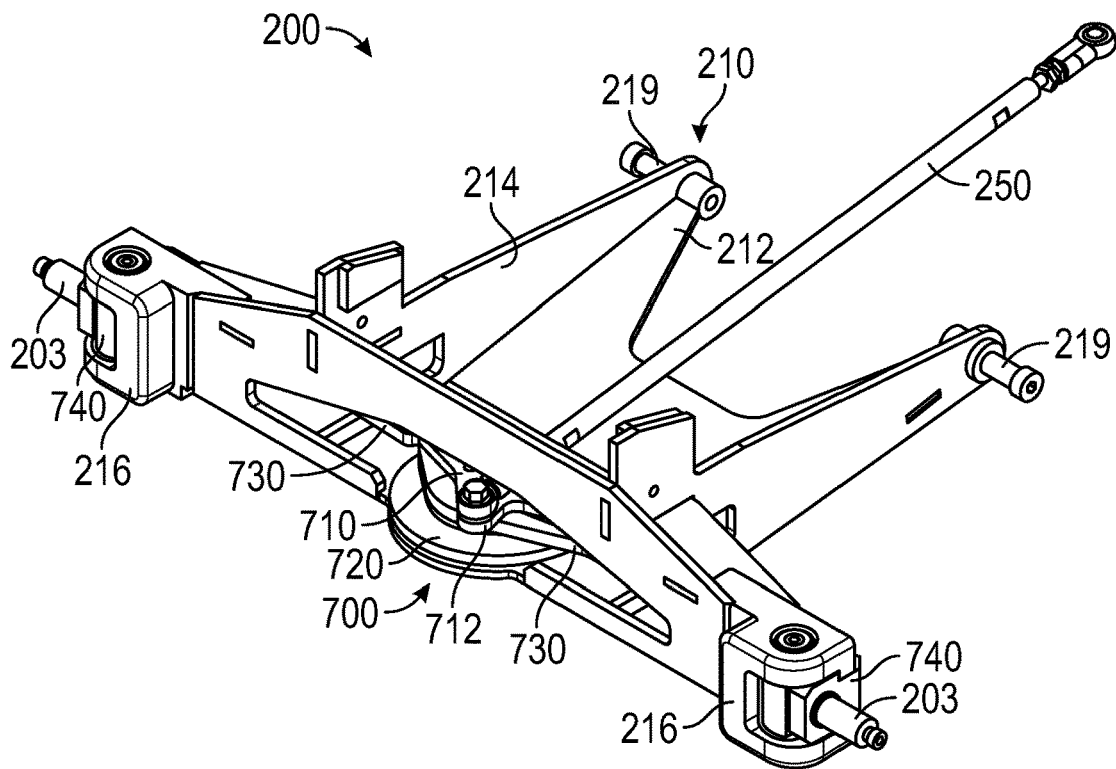
Figure 14B:
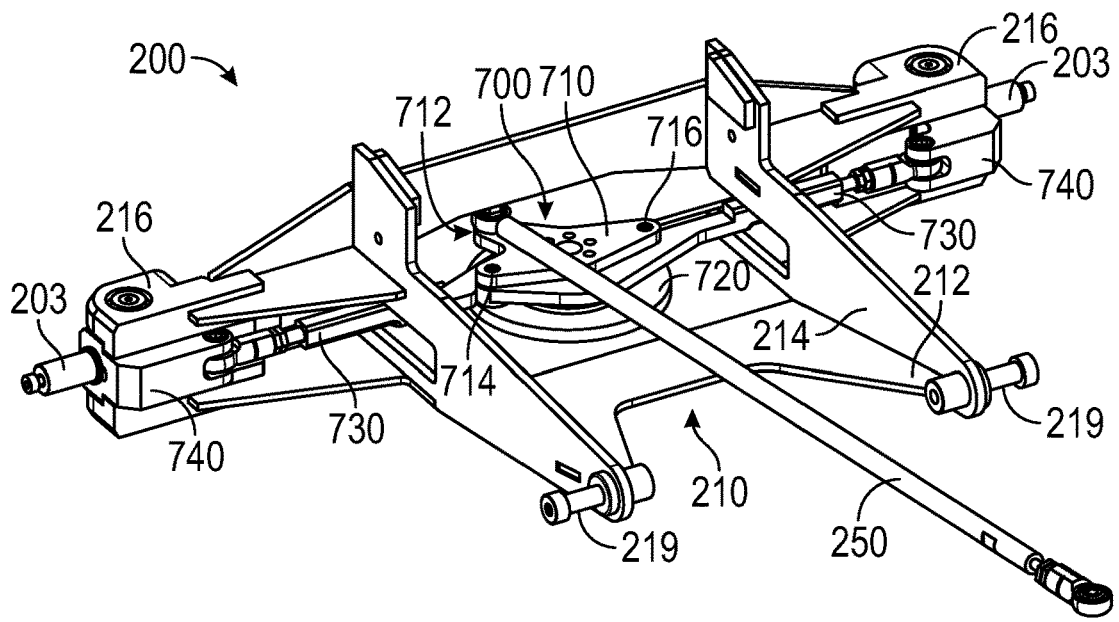
Figure 15B:
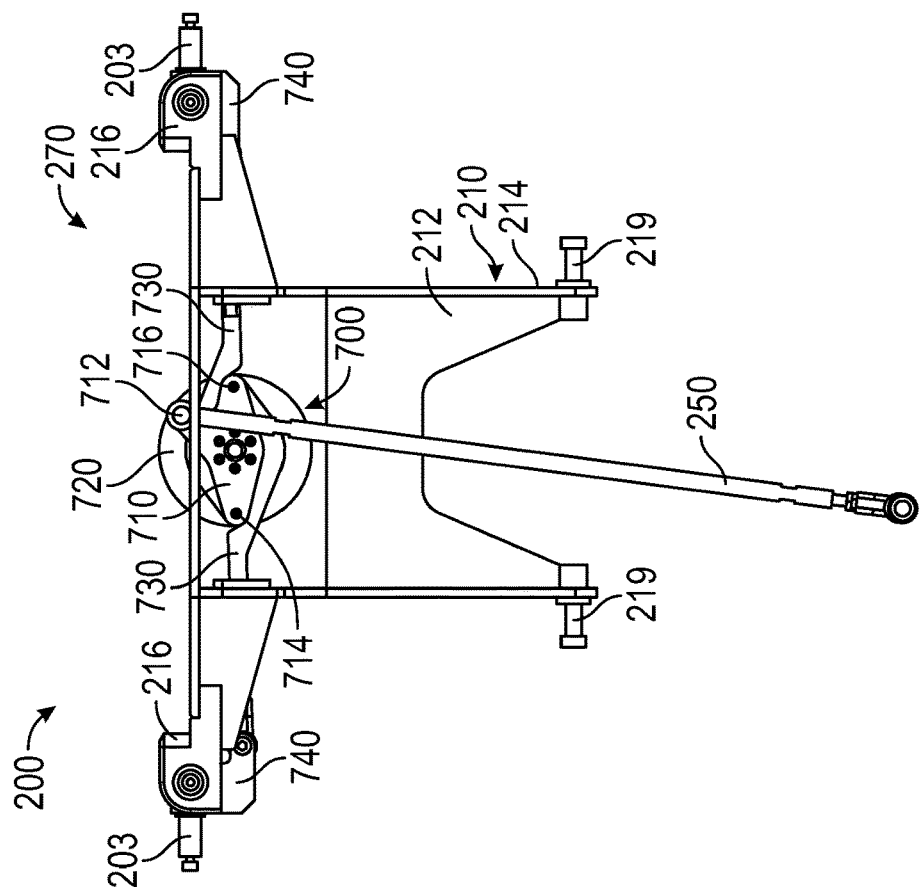
FIGS. 15A-15B are various views of the steering assembly of the surgical cart of FIG. 10 in a first configuration, according to an exemplary embodiment.
Figure 16B:
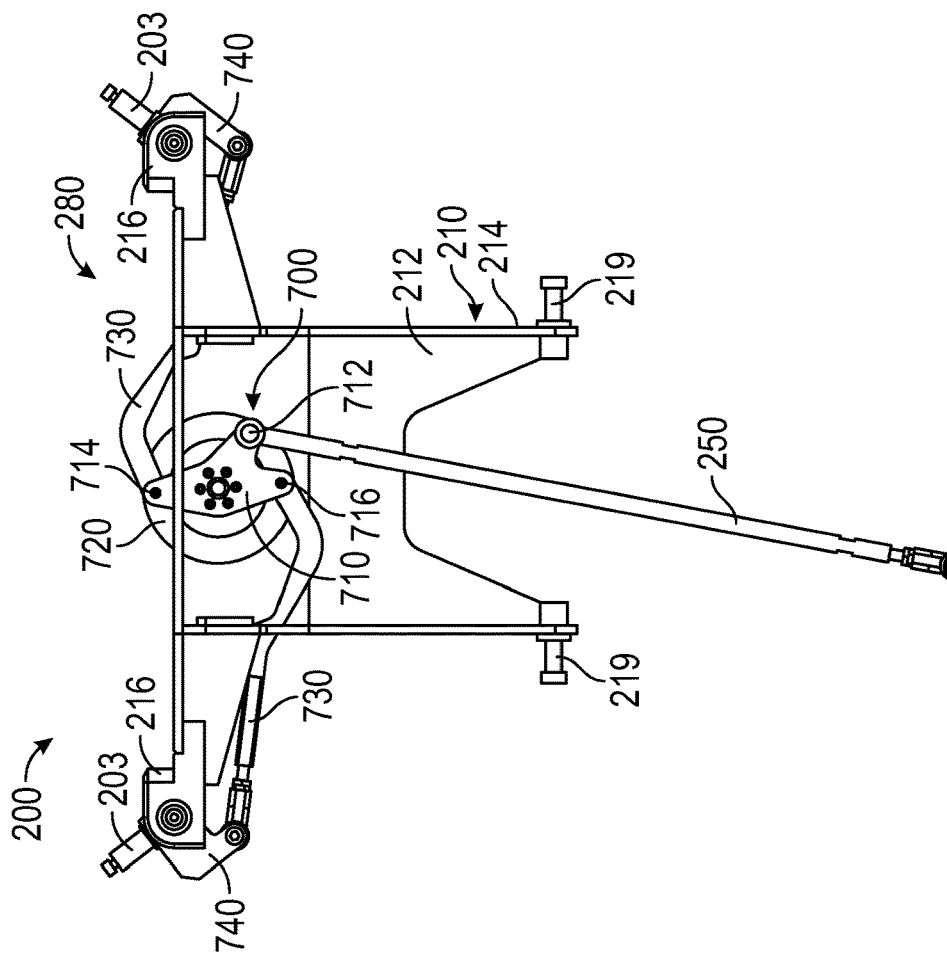
FIGS. 16A-16B are various views of the steering assembly of the surgical cart of FIG. 10 in a second configuration, according to an exemplary embodiment.
Figures 17A, 17B:
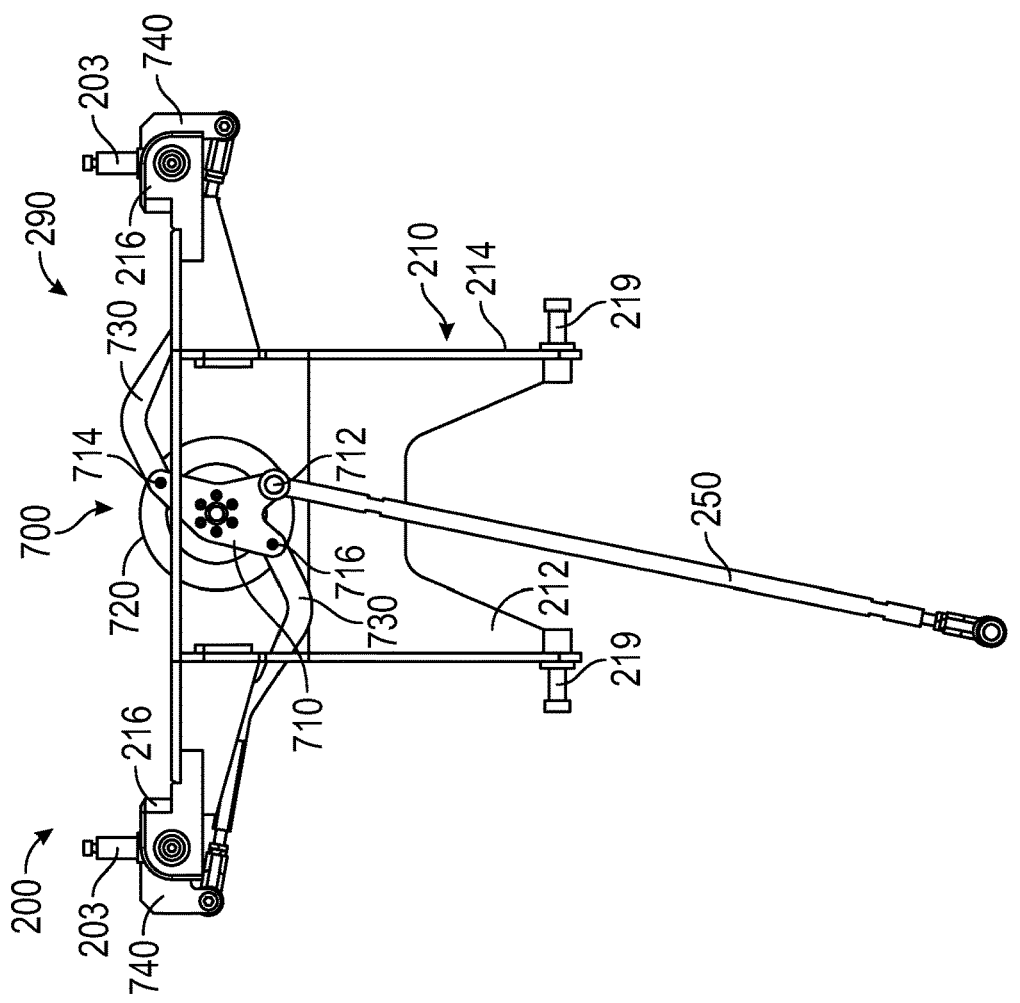
FIGS. 17A-17B are various views of the steering assembly of the surgical cart of FIG. 10 in a third configuration, according to an exemplary embodiment.

As shown in FIGS. 14B, 15B, 16B, and 17B, the cam 710 defines a first interface, shown as connecting linkage interface 712, a second interface, shown as first arm connection interface 714, and a third interface, shown as second arm connection interface 716. The opposing second end of the connecting linkage 250 couples to the connecting linkage interface 712, a first end of a first arm 730 couples to the first arm connection interface 714, and a first end of a second arm 730 couples to the second arm connection interface 716. As shown in FIGS. 14A-14B, the cam 710 is spaced from the rotor 720 such that the first end of the first arm 730 and the first end of the second arm 730 is positioned therebetween. As shown in FIGS. 14B, 15B, 16B, and 17B, an opposing second end of the first arm 730 is coupled to a first wheel joint 740 and an opposing second end of the second arm 730 is coupled to a second wheel joint 740. As shown in FIGS. 15B, 16B, and 17B, the wheel joints 740 are pivotably coupled to the wheel brackets 216. Accordingly, the rotation of the wheel joints 740 causes wheel axles 203 and thereby the front wheels 202 to rotate about the wheel axis 220 (see FIG. 13).

As shown in FIGS. 15B, 16B, and 17B, movement of the connecting linkage 250 (e.g., caused by the rotation of the handle 242, the handgrip 52, etc.) causes the cam 710 and the rotor 720 to rotate (e.g., about a central axis thereof, etc.). Such rotation may drive the arms 730 to extend laterally outward (e.g., through the wheel apertures 116, etc.), thereby driving the wheel joints 740 to rotate within the wheel brackets 216 to facilitate pivoting the front wheels 202 in various positions. According to an exemplary embodiment, the crank mechanism 700 (e.g., the rotor 720, the cam 710, etc.) is laterally offset relative to a longitudinal centerline of the surgical cart 10 (e.g., laterally biased towards one side, etc.). According to an exemplary embodiment, the first wheel joint 740 and the second wheel joint 740 have different characteristics (e.g., shapes, dimensions, configurations, etc.). According to an exemplary embodiment, the cam 710 has an asymmetric shape. The lateral offset of the crank mechanism 700, the asymmetry of the cam 710, and/or the different characteristics of the wheel joints 740 maintain the front wheels 202 in sync (e.g., the front wheels 202 do not pivot at different rates, angular rotation of the front wheels 202 is synchronized, etc.).

According to an exemplary embodiment, actuation of the handle 242 and/or the handgrip 52 corresponds with a 1:1 ratio of handle 242 and/or handgrip 52 rotation to front wheel 202 rotation (i.e., an amount of rotation of the handle 242 and/or the handgrip 52 directly corresponds with an amount of rotation of the front wheels 202). For example, a 45 degree turn of the handle 242 and/or the handgrip 52 corresponds with a 45 degree turn of the front wheels 202. In other embodiments, the amount of rotation of the handle 242 and/or the handgrip 52 does not directly correspond with the amount of rotation of the front wheels 202 (e.g., a 1:2 ratio, a 2:1 ratio, a 1:3 ratio; a 3:1 ratio; etc.). According to an exemplary embodiment, the steering mechanism 240 isolates external loads on the front wheels 202 from the handle 242 and/or the handgrip 52. In an alternative embodiment, the steering mechanism 240 steers the rear casters 302 and the front wheels 202 are free to rotate. In another alternative embodiment, the steering mechanism 240 steers at least one of the front wheels 202 and the rear casters 302. In yet another alternative embodiment, at least one of the front wheels 202 and the rear casters 302 are able to be both steered and free to rotate (i.e., the steering mechanism 240 is able to be selectively disengaged from the front wheels 202 and/or rear casters 302).

Figure 15A:
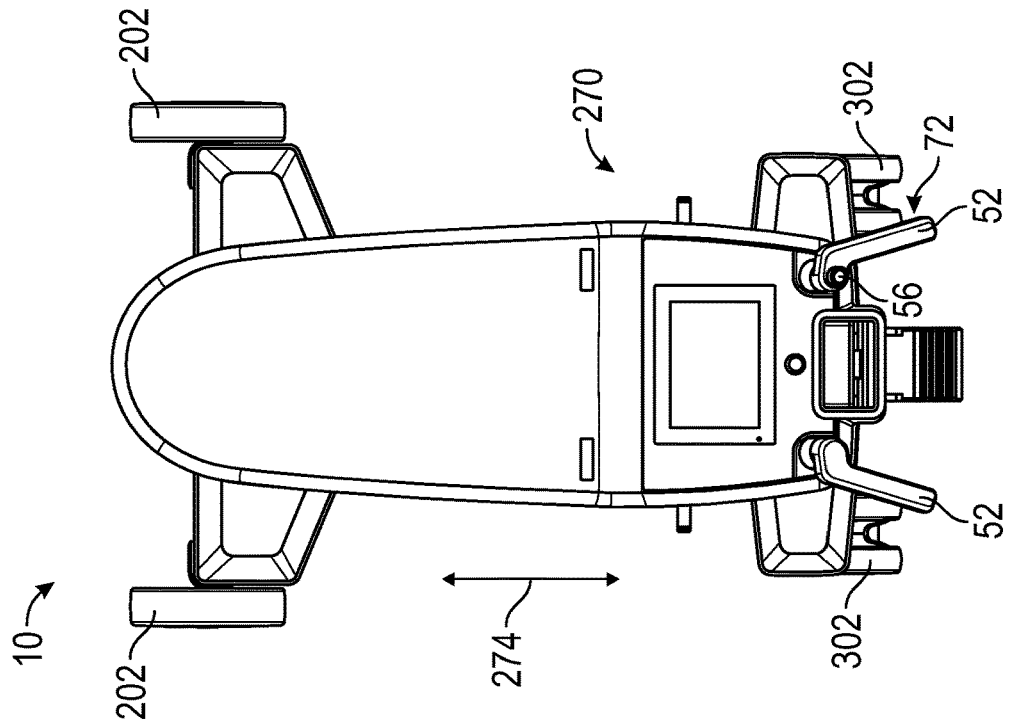

According to the exemplary embodiment shown in FIGS. 7A-7B and 15A-15B, the surgical cart 10 is configured in a first steering mode, shown as fore-and-aft steering mode 270. As shown in FIGS. 7A-7B, the handle 242 of the steering mechanism 240 is oriented in a first position, shown as fore-and-aft position 272, corresponding to the fore-and-aft steering mode 270. As shown in FIGS. 15A, the handgrip 52 is orientated in a first position, shown as fore-and-aft position 72. While the handle 242 is oriented in the fore-and-aft position 272 and/or the handgrip 52 is oriented in the fore-and-aft position 72, the front wheels 202 align such that they are parallel with the longitudinal axis of the surgical cart 10 (e.g., forward facing alignment, etc.). Thus, the surgical cart 10 is able to be maneuvered by an operator in a conventional way such as in a forward direction or a reverse direction, as indicated by directional arrow 274. Also, the surgical cart 10 is able to turn while moving forward or backward while in the fore-and-aft steering mode 270 since the rear casters 302 are free to rotate (e.g., about the vertical axis 340, etc.).

Figure 8B:
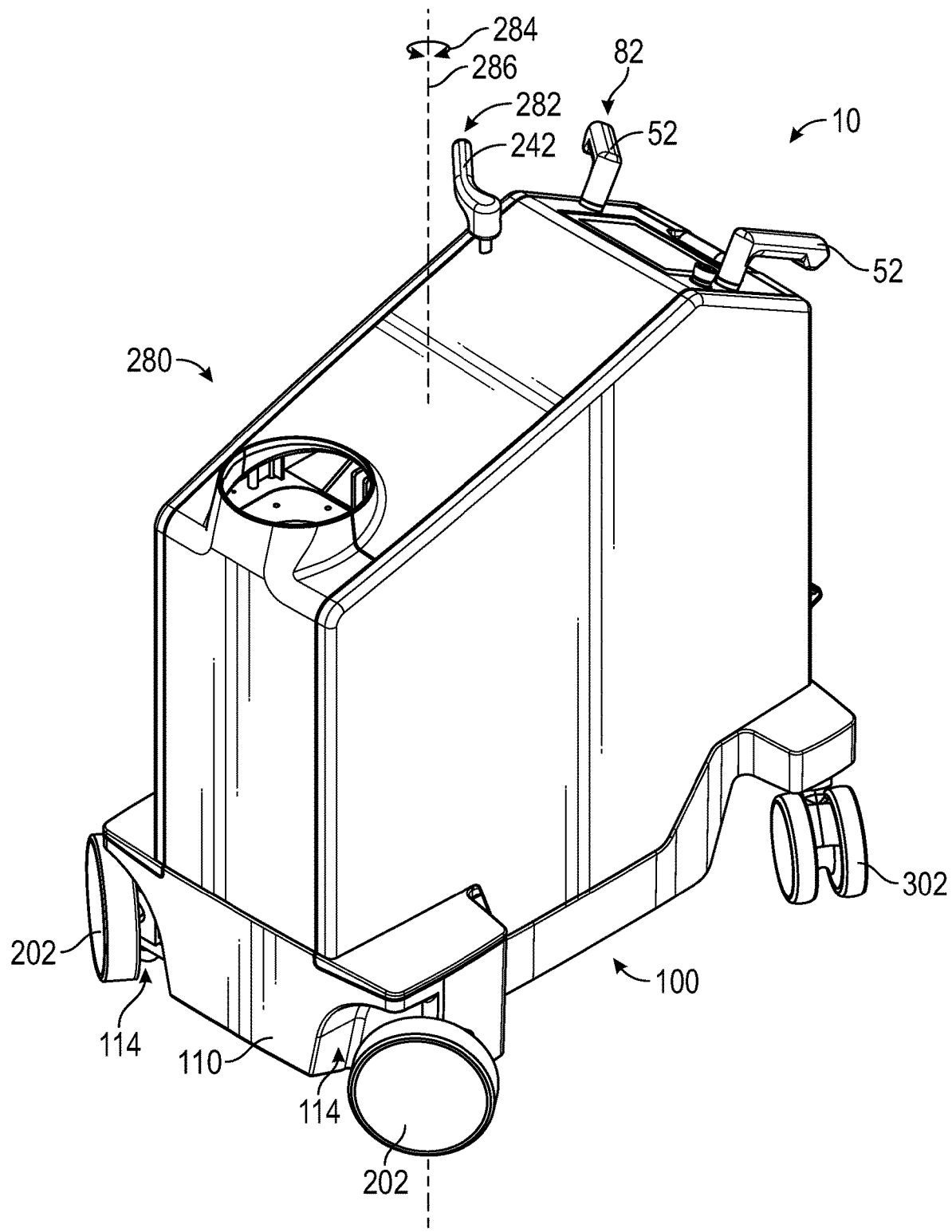
Figure 16A:
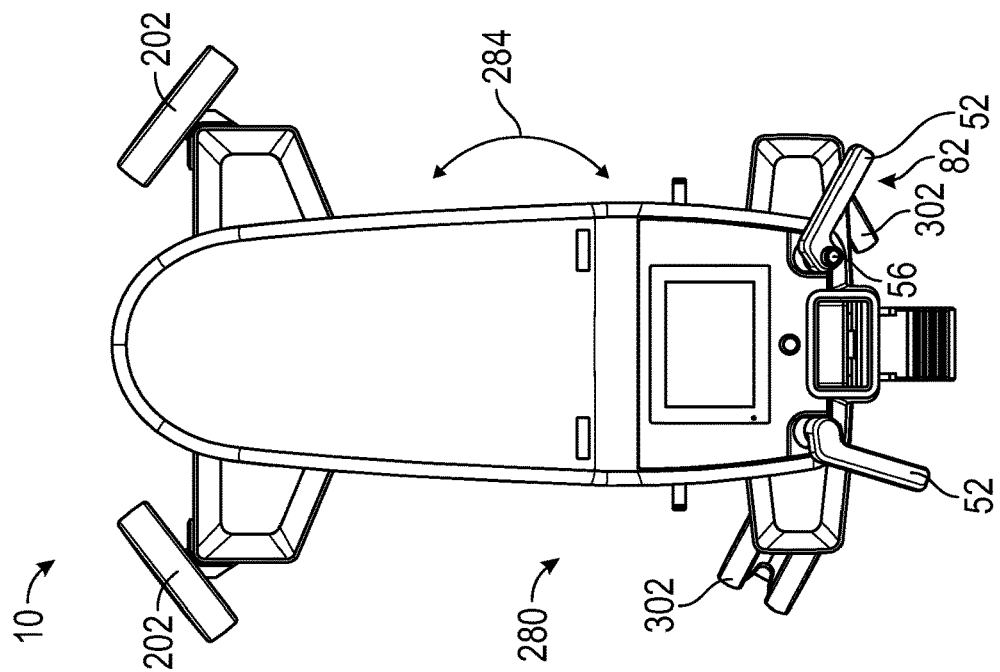

According to the exemplary embodiment shown in FIGS. 8A-8B and 16A-16B, the surgical cart 10 is configured in a second steering mode, shown as turn-on-axis steering mode 280. As shown in FIGS. 8A-8B, the handle 242 of the steering mechanism 240 is oriented in a second position, shown as turn-on-axis position 282, corresponding to the turn-on-axis steering mode 280 (e.g., the handle 242 is turned approximately 45 degrees from the fore-and-aft position 272, etc.). As shown in FIGS. 16A, the handgrip 52 is oriented in a second position, shown as turn-on-axis position 82, corresponding to the turn-on-axis steering mode 280 (e.g., the handgrip 52 is turned approximately 45 degrees from the fore-and-aft position 72, etc.). While the handle 242 is oriented in the turn-on-axis position 282 and/or the handgrip 52 is oriented in the turn-on-axis position 82, the front wheels 202 turn in towards the surgical cart 10 into a recess, shown as recess 114, defined by the front portion 110 of the chassis 100 (e.g., at an angle of approximately 45 degrees relative to the longitudinal axis of the surgical cart 10, etc.). Thus, the surgical cart 10 is able to be maneuvered by an operator in a rotational direction, as indicated by directional arrow 284, about a central axis 286 of the surgical cart 10. As shown in FIGS. 8A-8B and 16A, the rear caster 302 rotate accordingly when the surgical cart 10 is maneuvered while in the turn-on-axis steering mode 280 to facilitate a zero radius turn (i.e., the surgical cart 10 is rotatable in place about the central axis 286).

Figure 9B:
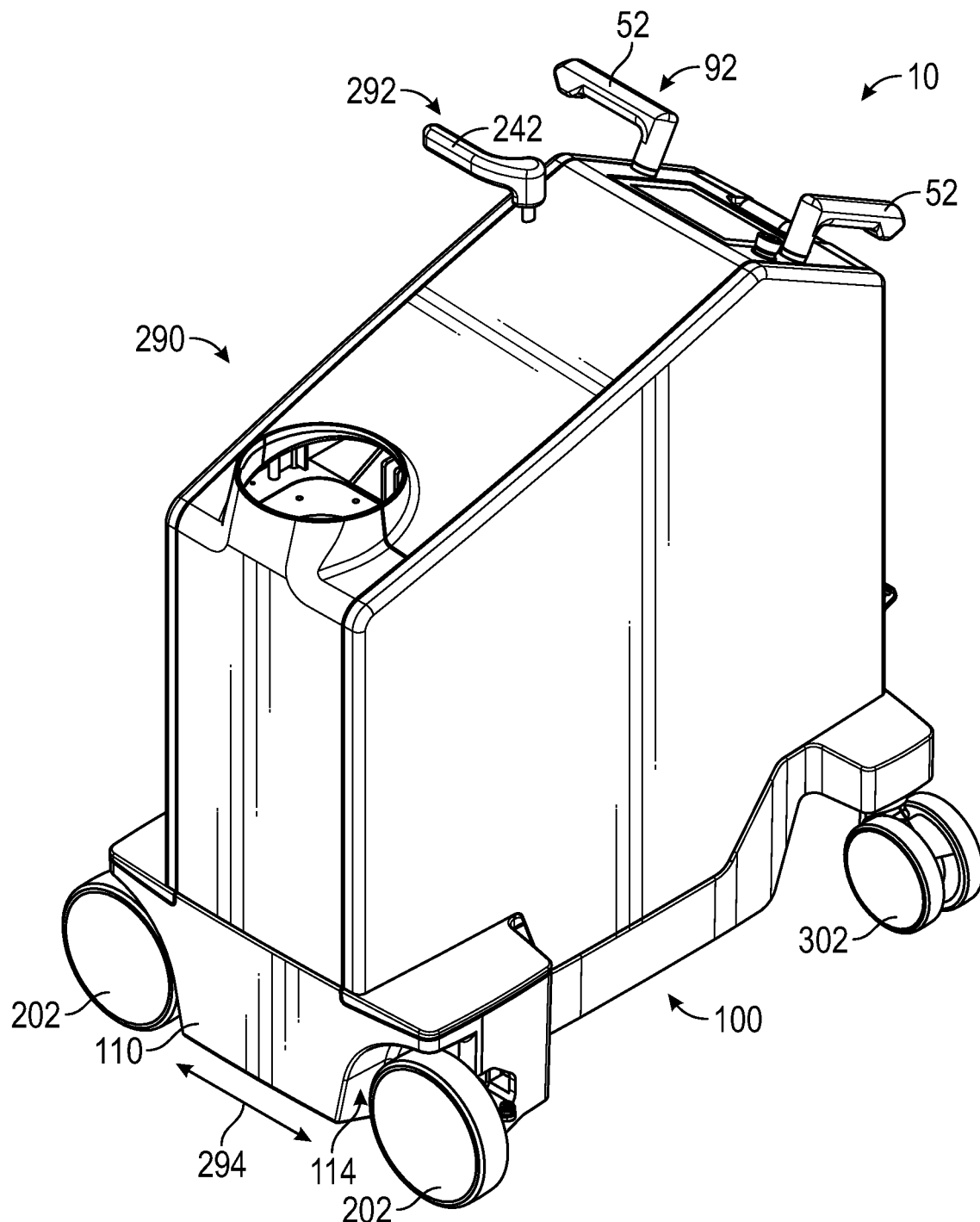
Figure 10:
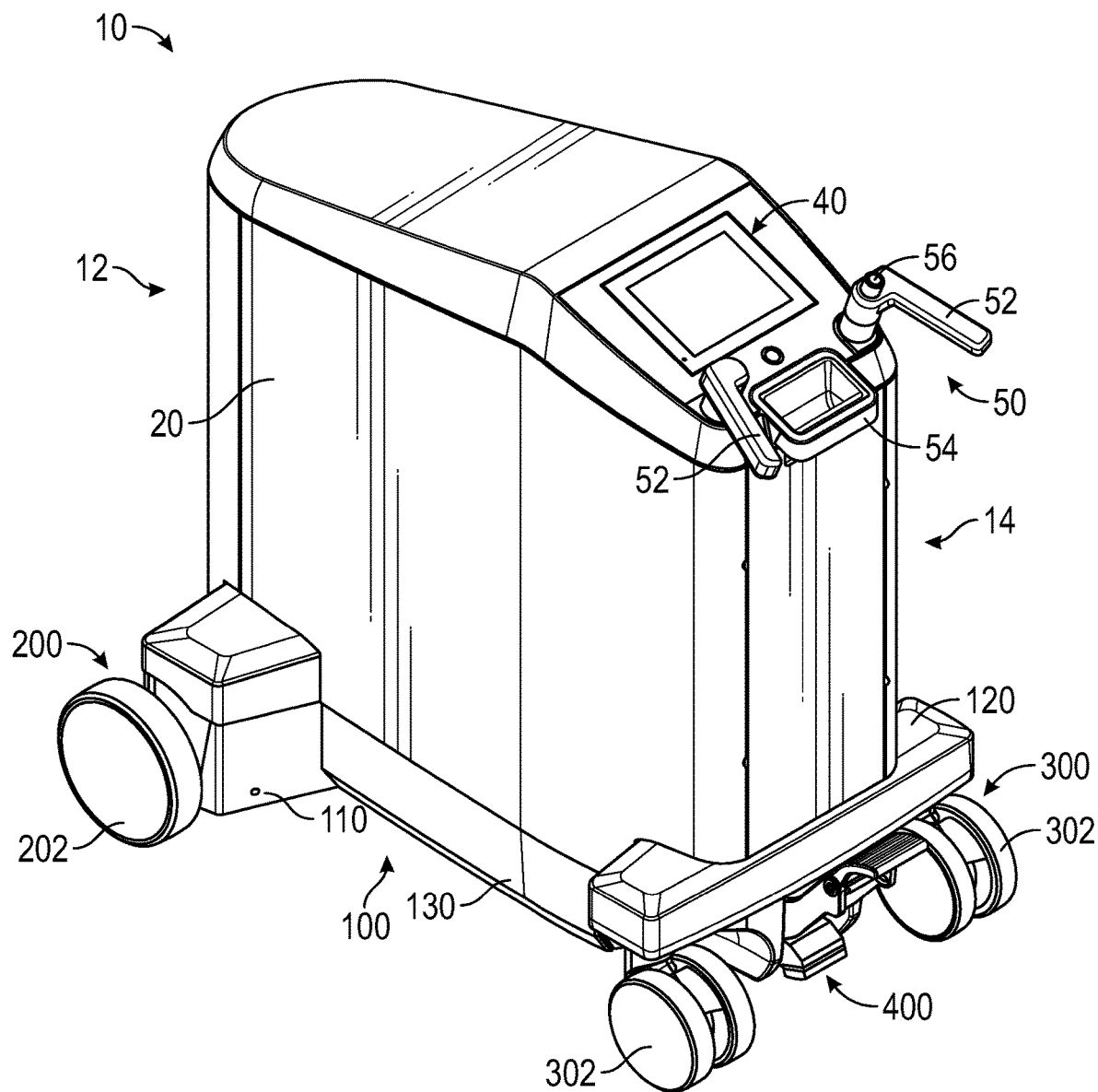
FIG. 10 is a rear perspective view of a surgical cart, according to another exemplary embodiment.

According to the exemplary embodiment shown in FIGS. 9A-9B and 17A-17B, the surgical cart 10 is configured in a third steering mode, shown as lateral steering mode 290. As shown in FIGS. 9A-9B, the handle 242 of the steering mechanism 240 is oriented in a third position, shown as lateral position 292, corresponding to the lateral steering mode 290 (e.g., the handle 242 is turned approximately 90 degrees from the fore-and-aft position 272, etc.). As shown in FIGS. 17A, the handgrip 52 is oriented in a third position, shown as lateral position 92, corresponding to the lateral steering mode 290 (e.g., the handgrip 52 is turned approximately 90 degrees from the fore-and-aft position 72, etc.). While the handle 242 is oriented in the lateral position 292 and/or the handgrip 52 is oriented in the lateral position 92, the front wheels 202 turn completely into the recesses 114 such the front wheels 202 are perpendicular to the longitudinal axis of the surgical cart 10 (e.g., at a 90 degree angle to the longitudinal axis of the surgical cart 10, etc.). Thus, the surgical cart 10 is able to be maneuvered by an operator in a lateral direction, as indicated by directional arrow 294.

As shown in FIGS. 9A-9B and 17A, the rear caster 302 rotate accordingly when the surgical cart 10 is maneuvered while in the lateral steering mode 290 to facilitate moving the surgical cart 10 laterally. Laterally maneuvering the surgical cart 10 may be useful following moving the surgical cart 10 (e.g., while in the fore-and-aft steering mode 270, etc.) into a surgical operating room to position the surgical cart 10 next to an operating table. Traditional surgical carts with fixed front wheels make this difficult. The cart has to be backed up, pivoted and moved back in. Sometimes this has to be repeated several times until the position is correct. This often requires handling the cart from the front end which may be in a sterile field of the operating room, which is not ideal. The surgical cart 10 of the present disclosure facilitates lateral translation at the operating table from the rear end 14 of the surgical cart 10 in a non-sterile field of an operating room. Further, the pivoting carriage assembly 300 facilitates evenly loading the front wheels 202 for controlled lateral translation.

Referring back to FIGS. 7B, 8B, and 9B, in an alternative embodiment, the handle 242 of the steering mechanism 240 is omitted and one of the handgrips 52 is mechanically coupled to the steering mechanism 240 to reconfigure the surgical cart 10 between the various steering modes (as described above in regards to FIGS. 15A, 16A, and 17A). In another alternative embodiment, each of the handgrips 52 independently controls the rotation of the front wheels 202 (e.g., the right handgrip 52 controls the pivoting of the right front wheel 202, the left handgrip 52 controls the pivoting of the left front wheel 202, one rotates clockwise and the other rotates counter-clockwise, etc.).

As shown in FIGS. 10, 15A, 16A, and 17A, the handgrip 52 (e.g., that controls the rotation of the front wheels 202, etc.) includes a push button, shown as lock button 56. In some embodiments, the lock button 56 is configured to facilitate locking the rotational position of the front wheels 202 (e.g., to prevent inadvertent rotation of the handgrip 52 and the front wheels 202, etc.). In some embodiments, the lock button 56 is configured to facilitate unlocking the rotational position of the front wheel 202 (e.g., a wheel lock for the front wheels 202 is biased into a locked position, etc.). In some embodiments, the position of the front wheels 202 automatically locks in one or more positions (e.g., when the handgrip 52 is oriented into the fore-and-aft position 72, etc.). As shown in FIG. 15A, the handgrips 52 are angled relative to a longitudinal axis of the surgical cart 10 (e.g., angled fifteen degrees relative to a longitudinal axis of the surgical cart 10, providing a better ergonomic feel when pushing the surgical cart 10, etc.).

The steering mechanism 240 herein is described in detail as being configured to facilitate selectively steering the front wheels 202 between the fore-and-aft position 272, the turn-on-axis positon 282, and the lateral position 292. However, it should be understood that the front wheels 202 may be selectively pivoted between and/or locked at any position between the fore-and-aft position 272 and the lateral position 292 (e.g., the front wheels 202 may be positioned and/or locked at any angle between zero and ninety degrees relative to a longitudinal axis of the surgical cart 10, etc.).

The term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, some elements shown as integrally formed may be constructed from multiple parts or elements, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Also two or more steps may be performed concurrently or with partial concurrence. Such variation will depend on various factors, including software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps. Other substitutions, modifications, changes, and omissions may be made in the design, operating conditions and arrangement of the exemplary embodiments without departing from the scope of the present disclosure.

What is claimed is:

1. A surgical robot, comprising:
a robotic device; and
a surgical cart coupled to the robotic device and comprising a body and a steering assembly coupled to the body;
wherein the steering assembly comprises a first wheel and a second wheel and is configured to be manually transitioned between a first mode and a second mode such that:
when the steering assembly is in the first mode, the steering assembly allows the cart to roll in a first linear direction; and
when the steering assembly is in the second mode, the steering assembly allows the cart to roll in a second linear direction perpendicular to the first linear direction,
wherein the steering assembly is configured to be manually transitioned from the first mode to the second mode by a user action mechanically causing rotation, in a first rotational direction, of the first wheel from being parallel to the first linear direction to being parallel to the second linear direction; and
the second wheel is mechanically linked to the first wheel such that the user action mechanically causing the rotation of the first wheel in the first rotational direction causes the second wheel to rotate in a second rotational direction opposite the first rotational direction.

2. The surgical robot of claim 1, wherein the steering assembly further is configured such that:
when the first mode is selected, the wheels are parallel with a longitudinal axis of the cart; and
when the second mode is selected, the wheels are perpendicular to the longitudinal axis of the cart.

3. The surgical robot of claim 2, wherein the cart further comprises an additional wheel, wherein the additional wheel is free to rotate about a vertical axis associated with the additional wheel.

4. The surgical robot of claim 1, wherein the wheels are nonparallel when a third mode is selected.

5. The surgical robot of claim 1, wherein the steering assembly further comprises a motor configured to steer the first wheel.

6. The surgical robot of claim 1, wherein the cart further comprises a motor configured to propel the cart.

7. The surgical robot of claim 1, further comprising an input device configured to receive a command to change between the first mode and the second mode.

8. A surgical cart, comprising:
a body; and
a steering assembly coupled to the body, comprising a first wheel and a second wheel, and configured to be manually transitioned between a first mode and a second mode such that:
when the steering assembly is in the first mode, the steering assembly allows the surgical cart to roll in a first linear direction; and
when the steering assembly is in the second mode, the steering assembly allows the surgical cart to roll in a second linear direction perpendicular to the first linear direction,
wherein:
the steering assembly is configured to be manually transitioned from the first mode to the second mode by a user action mechanically causing rotation, in a first rotational direction, of the first wheel from being parallel to the first linear direction to being parallel to the second linear direction; and
the second wheel is mechanically linked to the first wheel such that the user action mechanically causing the rotation of the first wheel in the first rotational direction causes the second wheel to rotate in a second rotational direction opposite the first rotational direction.

9. The surgical cart of claim 8, wherein the steering assembly is configured such that when the steering assembly is in a third mode, the steering assembly allows the surgical cart to roll in a rotational direction, the steering assembly is configured such that:
when the steering assembly is in the first mode and the second mode, the first wheel is parallel with the second wheel; and
when the steering assembly is in the third mode, the first wheel is non-parallel with the second wheel.

10. The surgical cart of claim 9, the steering mechanism further comprising a handle, a first linkage coupled to the first wheel such that the first wheel is coupled to the handle via the first linkage, and a second linkage coupled to the second wheel such that the second wheel is coupled to the handle via the second linkage, wherein the first linkage crosses the second linkage.

11. The surgical cart of claim 8, further comprising a motor configured to propel the surgical cart.

12. The surgical cart of claim 8, further comprising an input device configured to receive a command to change between the first mode and the second mode.

13. The surgical cart of claim 12, wherein the input device is a handle of the steering assembly.

14. The surgical cart of claim 12, further comprising a motor and a computing system, wherein the computing system is programmed to cause the motor to transition the steering assembly between the first mode and the second mode in response to the command.

15. A surgical cart, comprising:
a body; and
a steering assembly coupled to the body and configured such that:
when the steering assembly is in a first mode, the steering assembly allows the surgical cart to roll in a first linear direction; and
when the steering assembly is in a second mode, the steering assembly allows the surgical cart to roll in a pivoting direction;
wherein the steering assembly comprises a first wheel and is configured to be manually transitioned from the first mode to the second mode by a user action mechanically causing rotation, in a first direction, of the first wheel;
wherein the steering assembly comprises a second wheel, wherein the second wheel is mechanically linked to the first wheel such that the user action mechanically causing the rotation of the first wheel in the first direction causes the second wheel to rotate in a second direction opposite the first direction.

* * * * *